US006821985B2

United States Patent
Chenard et al.

(10) Patent No.: US 6,821,985 B2
(45) Date of Patent: Nov. 23, 2004

(54) PHARMACEUTICAL COMBINATIONS FOR THE TREATMENT OF STROKE AND TRAUMATIC BRAIN INJURY

(75) Inventors: Bertrand L. Chenard, Waterford, CT (US); Frank S. Menniti, Mystic, CT (US); Mario D. Saltarelli, Mystic, CT (US)

(73) Assignee: Pfizer, Inc., New York, NY (US)

( * ) Notice: Subject to any disclaimer, the term of this patent is extended or adjusted under 35 U.S.C. 154(b) by 25 days.

(21) Appl. No.: 09/947,878

(22) Filed: Sep. 6, 2001

(65) Prior Publication Data

US 2002/0123510 A1 Sep. 5, 2002

Related U.S. Application Data

(60) Provisional application No. 60/230,943, filed on Sep. 6, 2000.

(51) Int. Cl.[7] .................. A61K 31/44; A61K 31/445
(52) U.S. Cl. .................. 514/304; 514/319; 514/320; 514/327
(58) Field of Search ................ 514/304, 319, 514/320, 327

(56) References Cited

U.S. PATENT DOCUMENTS

| | | |
|---|---|---|
| 5,272,160 A | 12/1993 | Chenard |
| 5,338,754 A | 8/1994 | Chenard ............. 514/422 |
| 5,356,905 A | 10/1994 | Butler |
| 5,741,819 A | 6/1995 | Illig et al. ............. 514/602 |
| 5,604,260 A | 2/1997 | Guay et al. |
| 5,861,510 A | 1/1999 | Piscopio et al. |
| 5,942,540 A | 8/1999 | Kozachuk |
| 5,976,530 A | 11/1999 | Haigwood et al. ....... 426/94.64 |
| 6,350,739 B1 * | 2/2002 | Simpkins et al. ........... 514/182 |

FOREIGN PATENT DOCUMENTS

| | | |
|---|---|---|
| EP | 0606046 | 8/1997 |
| WO | WO96/06081 | 5/1995 |
| WO | WO 9625948 | 8/1996 |
| WO | WO 9637222 | 11/1996 |
| WO | WO 9736871 | 10/1997 |
| WO | WO 9925353 | 5/1999 |

OTHER PUBLICATIONS

Constantino Iadecola, et al., Inhibition of Inducible Nitric Oxide Synthase Ameliorates Cerebral Ischemic Damage, 1995, Am. J. Physiol. (Regul.), 37, pp. R286–R292.
Jane R. Connor, et al., Suppression of Adjuvant–Induced Arthritis by Selectiveinhibition of inducible Nitric Oxided Synthase, European Journal of Pharmacology 273, (1993) 15–24.

P.K. Moore et al., Characterization of the Novel Nitric Oxide Synthase Inhibitor 7–nitro Indazole and Related Indazoles: Antinocicpive and Cardiovascular effects, Br. J. Pharmacol. (1993),,110, 219–224.
Tazuka Yoshida et al., The NOS inhibitor, 7–Nitroindazole, Decreases Focal Infarct Volume but not the Response to Topical Acetylcholine in Pial Vessels, Journal of Cerebral Blood Flow and Metabolism, vol. 14, pp. 924–929, 1994.
Norifumi Yonehara et al., Nitric Oxide in the Rat Spinal Cord in Freund's Adjuvant–Induced Hyperalgesia, Jpn. J. Pharmacol. 75, 327–335, 1997.
Hannah Monyer et al., Heteromeric NMDA Receptors: Molecular and Functional Distinction of Subtypes, Science, vol. 256, pp. 1217, 1992.
B. L. Chenard et al., Antagonists Selective for NMDA Receptors Containing the NR2B Subunit, Current Pharmaceutical Design, 1999, 5, 381–404.
Frank Menniti et al., CP–101,606, A Potent Neuroprotectant Selective for Forebrain Neurons, European Journal of Pharmacology 331, (1997), 117–126.
Peter Bentzer et al., Prostacyclin Reduces Microvascular Fluid Conductivity in Cat Skeletal Muscle through Opening of ATP–Dependent Potassium Channels, J. Vasc. Res. 1999:36:516–523.
B. L. Chenard et al., Separation of $d_1$ Adrenergic and N–Methyl–D–aspartate Antagonist Activity in a Series of Ifenprodil Compounds, J. Med. Chem. 1991, 34, 3085–3090.
Keith W. Muir et al., Clinical Experience with Excitatory Amino Acid Antagonist Drugs, Stroke, vol. 26, pp. 503–513, No. 3, 1995.
J. McCulloch, Glutamate Receptor Antagonist in Cerebral Ischaemia, J. Neural. Transm. (1994) [Supp] 43:71–79.
John A. Kemp et al., The Glycine Site of the NMDA Receptor–five years on, TiPS, 1993, pp. 20–25, vol. 14.

* cited by examiner

Primary Examiner—Raymond J. Henley, III
(74) Attorney, Agent, or Firm—Peter C. Richardson; Andrea F. Dorigo

(57) ABSTRACT

This invention relates to methods of treating traumatic brain injury (TBI) or hypoxic or ischemic stroke, comprising administering to a patient in need of such treatment an NR2B subtype selective N-methyl-D-aspartate (NMDA) receptor antagonist in combination with either: (a) a sodium channel antagonist; (b) a nitric oxide synthase (NOS) inhibitor; (c) a glycine site antagonist; (d) a potassium channel opener; (e) an AMPA/kainate receptor antagonist; (f) a calcium channel antagonist; (g) a GABA-A receptor modulator (e.g., a GABA-A receptor agonist); or (h) an antiinflammatory agent. This invention also relates to methods of treating hypoxic or ischemic stroke comprising administering to a patient in need of such treatment an NMDA receptor antagonist in combination with a thrombolytic agent.

11 Claims, No Drawings

PHARMACEUTICAL COMBINATIONS FOR THE TREATMENT OF STROKE AND TRAUMATIC BRAIN INJURY

This application claims priority under 35 U.S.C. 119(e) of U.S. Provisional Application No. 60/230,943, filed Sep. 6, 2000.

BACKGROUND OF THE INVENTION

This invention relates to methods of treating traumatic brain injury (TBI) or ischemic or hypoxic stroke, comprising administering to a patient in need of such treatment an NR2B subtype selective N-methyl-D-aspartate (NMDA) receptor antagonist in combination with one or more other compounds that protect neurons from toxic insult, inhibit the inflammatory reaction after brain damage or promote cerebral reperfusion.

More specifically, this invention relates to methods of treating traumatic brain injury (TBI) or hypoxic or ischemic stroke, comprising administering to a patient in need of such treatment an NR2B subtype selective N-methyl-D-aspartate (NMDA) receptor antagonist in combination with either: (a) a sodium channel antagonist; (b) a nitric oxide synthase (NOS) inhibitor; (c) a glycine site antagonist; (d) a potassium channel opener; (e) an AMPA/kainate receptor antagonist; (f) a calcium channel antagonist; (g) a GABA-A receptor modulator (e.g., a GABA-A receptor agonist); (h) an antiinflammatory agent; or (i) a matrix metalloprotease (MMP) inhibitor.

This invention also relates to methods of treating hypoxic or ischemic stroke comprising administering to a patient in need of such treatment an NR2B subtype selective NMDA receptor antagonist in combination with a thrombolytic agent.

Brain and spinal cord injury caused by stroke, trauma or hypoxia often result in lifelong disability and premature death. The cause of disability and death is the disruption of function and frank death of neurons and other cells in the central nervous system. Therefore, a clear benefit is anticipated from therapies that reduce or prevent neuronal dysfunction and death after ischemic, hypoxic or traumatic CNS insult.

One of the causes of neuronal dysfunction and death after CNS insult is toxicity caused by a prolonged elevation of glutamate and other excitatory amino acids (EAAs) and overactivation of the N-methyl-D-aspartate (NMDA) subtype of glutamate receptors. Glutamate and other EAAs play dual roles in the central nervous system as essential amino acids and the principal excitatory neurotransmitters. There are at least four classes of EAA receptors, specifically NMDA, AM PA (2-amino-3-(methyl-3-hydroxyisoxazol-4-yl)propanoic acid), kainate and metabotropic. These EAA receptors mediate a wide range of signaling events that impact all physiological brain functions. As neurotransmitters, EAAs are released from postsynaptic nerve terminals and then are rapidly resequestered by a variety of cellular reuptake mechanisms. Consequently, the physiological levels of EAAs in the brain parenchyma are maintained at a low level. However, after a CNS insult, the levels of EAAs in the parenchyma increase dramatically and may remain elevated for periods of hours to days. This results in pathological overactivation of EAA receptors and neuronal dysfunction and death.

Several lines of evidence suggest that the NMDA subtype of glutamate receptor is the principal mediator of the EAA-induced toxicity described above. Neurons in primary culture are exquisitely sensitive to the toxic effects of NMDA receptor activation and NMDA receptor antagonists protect cultured neurons from both NMDA and glutamate toxicity (Choi et al., *J. Neurosci.*, 1988, 8, 185–196; Rosenberg et al., 1989, *Neurosci. Lett.* 103, 162). NMDA receptors are also implicated as mediators of neurotoxicity in vivo since NMDA receptor antagonists can reduce neuron loss in animal models of focal ischemia (McCulloch, *J. Neural. Trans.*, 1994, 71–79) and head trauma (Bullock et al., *Acta Neurochir.*, 1992, 55, 49–55). The neuroprotective effect of NMDA receptor inhibition is realized with several different classes of compounds that target different sites on the NMDA receptor-channel complex. These include competitive antagonists at the glutamate binding site such as (R,E)-4-(3-phosphonoprop-2-enyl) piperazine-2-carboxylic acid (d-CPPene) (Lowe et al., 1994, *Neurochem Int.* 25, 583) and cis-4-phosphonomethyl-2-piperidine carboxylic acid (CGS-19,755) (Murphy et al., 1988, *Br. J. Pharmacol.* 95, 932) and competitive antagonists at the glycine co-agonist (Johnson et al., *Nature*, 1987, 327, 529–531; and Kemp et al., *Trends Pharmacol. Sci.*, 1993, 14, 20–25) binding site such as 5,7-dichloro-4S-(3-phenyl-ureido)-1,2,3,4-tetrahydroquinoline-2R-carboxylic acid (L-689,560) and 5-nitro-6,7-dichloro-1,4-dihydro-2,3-quinoxalinedione (ACEA-1021) (Leeson et al., 1994, *J. Med. Chem.* 37, 4053). Compounds have also been identified which block the NMDA receptor-gated ion channel, including phencyclidine (PCP), (+)-5-methyl-10,11-dihydro-5-H-dibenzo[a,d]cycloheptan-5,10-imine (MK-801) (Kemp et al., 1987, *Trends in Neurosci.* 10, 294), and C-(1-napthyl-N'-(3-ethyl phenyl)-N'-methyl guanidine hydrochloride (CNS-1102) (Reddy et al., 1994, *J. Med. Chem.* 37, 260).

The neuroprotective effect of NMDA receptor antagonists in experimental systems has prompted considerable interest in the therapeutic potential of this type of compound. Several prototype antagonists have been progressed into clinical trials, especially for stroke and head trauma (Muir et al., 1995, *Stroke* 26, 503–513). However, side effects at therapeutic drug levels have been a significant problem that has hindered the development process (Muir et al., supra). In particular, both glutamate competitive antagonists and channel blocking agents cause cardiovascular effects and psychotic symptoms in man. Although the physiological basis for these side effects are not yet understood, in rodents these types of compounds also cause locomotor hyperactivity and a paradoxical neuronal hyperexcitability manifest as neuronal vacuolization in cingulate and retrosplenial cortices (Olney et al., 1991, *Science*, 254, 1515–1518). Antagonists at the glycine coagonist site cause less locomotor activation and do not cause neuronal vacuolization at neuroprotective doses in rodents, suggesting that this class of antagonists may be better tolerated in man (Kemp et al., 1993, *Trends Pharmacol. Sci.* 14, 20–25). Unfortunately, physicochemical problems associated with the quinoxalinedione nucleus (solubility, brain penetration, protein binding) have hindered efforts to bring this class forward in the clinic.

The compound (1S,2S)-1-(4-hydroxyphenyl)-2-(4-hydroxy-4-phenylpiperidino)-1-propanol) (hereinafter referred to as "Compound A") represents a fourth mechanistic class of NMDA receptor antagonist. This class is unique in that it is specific for a subtype of NMDA receptor, those containing the NR2B subunit that is expressed in the forebrain. As with other ligand gated ion channels, the functional NMDA receptor is composed of multiple protein subunits. Five subunits have been cloned to date, NR1 (of which there are eight splice variants) and NR2A-D. Expression studies indicate a composition of at least one NR1 subunit and one or more of the NR2 subunits (Monyer et al., Science, 1992, 256, 1217–1221; Kutsuwada et al., 1992, Nature 358, 36; and Chazot et al., 1994, J. Biol. Chem. 269, 24403). In situ hybridization and immunohistochemistry studies indicate that subunits are widely and differentially distributed throughout the brain (Monyer et al, Neuron, 1994, 12, 529–540; Kutsuwada et al., supra; Ishii et al., 1993, J. Biol Chem. 268, 2836; Wenzel et al., 1995, NeuroReport 7, 45).

Compound A and other structurally related compounds have been found to be functionally selective for NMDA receptors containing the NR2B subunit. The fact that this class of NMDA receptor antagonist is neuroprotective in a variety of in vitro and in vivo experimental models (Di et al., 1997, Stroke 28, 2244–2251; Okiyama et al., 1998, Brain Res. 792, 291–298; Okiyama et al., 1997, J. Neurotrauma 14, 211–222; Tsuchida et al., 1997, Neurotrama 14, 409–417) suggests that NR2B subunit containing NMDA receptors are prominently involved in the EAA-induced toxic cascade. Furthermore, antagonists selective for NR2B subunit containing NMDA receptors have been found to produce less toxic side effects in animals and in man than other classes of NMDA receptor antagonists and can be selected for excellent pharmaceutical properties. Thus, certain cardiovascular and behavioral adverse side effects that are exhibited upon administration of therapeutically effective dosages of subunit nonselective NMDA receptor antagonists can be eliminated or significantly reduced by the use, in therapeutically effective dosages, of NR2B subtype selective NMDA receptor antagonists. The NMDA antagonists employed in the methods and pharmaceutical compositions of the present invention are preferably those that exhibit selectivity for the NR2B subunit containing NMDA receptors.

Selectivity of compounds for the $NR^2B$-subunit containing NMDA receptor is defined as an affinity for the racemic $[^3H](+)$-(1S, 2S)-1-(4-hydroxy-phenyl)-2-(4-hydroxy-4-phenylpiperidino)-1-propanol binding site in forebrain of rats, as described by Chenard and Menniti (Antagonists Selective for NMDA receptors containing the $NR^2B$ Subunit, Current Pharmaceutical Design, 1999, 5:381–404). This affinity is assessed in a radioligand binding assay as described later in this application. Selective compounds are those which displace specific binding of racemic $[^3H]$CP-101,606 from rat forebrain membranes with an $IC_{50} \leq 5$ $\mu$M.

A number of the compounds with selectivity for the NR2B subtype of NMDA receptor also interact with and inhibit a number of other receptors and ion channels. For example, ifenprodil inhibits the a, adrenergic receptor with an affinity similar to that at which the compound inhibits NR2B subtype NMDA receptors. Inhibition of $\alpha_1$ adrenergic receptors is related to particular structural features of ifenprodil and related molecules (Chenard, et at., J. Med. Chem., 1991, 34, 3085–3090 (1991). It is well known that compounds that block $\alpha_1$ adrenergic receptors (prazosin, for example) are associated with blood pressure lowering actively, an activity that is contraindicated for drugs used treat stroke, TBI and related conditions. Therefore, the NMDA antagonists employed in the methods and pharmaceutical compositions of the present invention preferably are those that exhibit selectivity for the NR2B subunit containing NMDA receptors over that for $\alpha_1$ adrenergic receptors, specifically, those having a ratio of NR2B receptor selectivity to $a_1$ adrenergic receptor selectivity of at least about 3:1. More preferably, such ratio is at least 5:1.

The present invention relates to the additional therapeutic benefits that may be gained by treating traumatic brain injury, stroke, or hypoxic brain injury with an NR2B subtype selective NMDA receptor antagonist in combination with other types of compounds. These include compounds that protect neurons from toxic insult, inhibit the inflammatory reaction after brain damage and/or promote cerebral reperfusion. Although NMDA receptor-mediated toxicity is a principal cause of the neuronal dysfunction and death that occurs after CNS insult, additional mechanisms also participate. By reducing the pathological consequences of these additional mechanisms, the overall benefit of the therapeutic intervention may be increased. Furthermore, inhibiting multiple pathological processes may provide an unexpected synergistic benefit over and above that which may be achievable alone with the use of an NMDA receptor antagonist.

During the course of an ischemic, hypoxic, or traumatic injury to the CNS a number of toxic products are formed which can further damage brain cells injured by the primary pathological process or produce damage in cells that otherwise escape damage from the primary insult. These toxins include, but are not limited to: nitric oxide (NO); other reactive oxygen and nitrogen intermediates such as superoxide and peroxynitrite; lipid peroxides; TNF$\alpha$, IL-1 and other interleukins, cytokines or chemokines; cyclooygenase and lipoxygenase derivatives and other fatty acid mediators such as leukotrienes, glutamate and prostaglandins; and hydrogen ions. Inhibiting the formation, action or accelerating the removal of these toxins may protect CNS cells from damage during an ischemic, hypoxic or traumatic injury. Furthermore, the beneficial effects of inhibiting the formation, action or accelerating the removal of these toxins may be additive or synergistic with the benefits of inhibiting NR2B subunit containing NMDA receptors with a NR2B subunit selective NMDA receptor antagonist. Examples of compounds that inhibit the formation or action of these toxins, or accelerate their removal include, but are not limited to, antioxidants, sodium channel antagonists, NOS inhibitors, potassium channel openers, glycine site antagonists, potassium channel openers, AMPA/kainate receptor antagonists, calcium channel antagonists, GABA-A receptor modulators (e.g., GABA-A receptor agonists), and antiinflammatory agents.

The formation and release of many of the toxins listed above are triggered by physiological signaling mechanisms that become pathologically activated by ischemic, hypoxic or traumatic CNS injury. Activation of these signaling mechanisms can also result in cellular depolarization. This depolarization may disrupt cellular ionic homeostasis, accelerate the rate of energy utilization as the cell strives to maintain homeostasis, and/or further accelerate the rate of formation and release of toxins. Thus, inhibition of these signaling mechanisms during ischemic, hypoxic or traumatic CNS injury may reduce the degree of cellular dysfunction and death. Furthermore, the beneficial effects of inhibiting these signaling mechanisms may be additive or synergistic with the benefits of inhibiting NR2B subunit containing NMDA receptors with a NR2B subunit selective NMDA receptor antagonist. These signaling mechanisms include, but are not limited to: NMDA receptors other than those containing the NR2B subunit; other EAA receptors such as AMPA, KA, or metabotropic receptors; other ligand-gated ion channels which promote depolarization and/or toxin release; voltage gated calcium channels including those of the L-, P-, Q/R-, N-, or T-types; voltage gated sodium channels. Examples of compounds that inhibit these signaling pathways include, but are not limited to, AMPA/kainate receptor antagonists, sodium channel antagonists and calcium channel antagonists.

Another approach to inhibiting cellular depolarization caused by ischemic, hypoxic or traumatic CNS injury and the resultant deleterious effects is to activate signaling pathways that oppose those causing depolarization. Again, the beneficial effects of activating these signaling mechanisms may be additive or synergistic with the benefits of inhibiting NR2B subunit containing NMDA receptors with a NR2B subunit selective NMDA receptor antagonist. These signaling mechanisms include, but are not limited to: GABA$_A$ receptor activation; voltage or ligand gated potassium channel activation; voltage or ligand gated chloride channel activation. Examples of compounds that activate these signaling pathways include, but are not limited to, potassium channel openers and GABA-A receptor agonists.

Excessive cellular depolarization and the loss of ionic homeostasis can lead to the loss in the ability of a cell to maintain physical integrity and cellular death ensues by a process often termed necrotic cell death. However, ischemic, hypoxic or traumatic CNS injury can also induce in many cells the activation of another mechanism causing cellular death that is termed apoptosis. The relationship between necrotic and apoptotic cell death is not fully understood and in pathological conditions such as ischemic, hypoxic or traumatic CNS injury both necrotic and apoptotic mechanisms leading ultimately toward cell death may be at play. Regardless of the specifics of this interrelationship, it has been suggested that inhibition of apoptotic mechanism of cell death may have a therapeutic benefit in ischemic, hypoxic or traumatic CNS injury. The beneficial effects of inhibiting apoptosis during ischemic, hypoxic or traumatic CNS injury may be additive or synergistic with the benefits of inhibiting NR2B subunit containing NMDA receptors with a NR2B subunit selective NMDA receptor antagonist. Apoptotic mechanisms include, but are not limited to: activation of FASTNFα/p75 receptors; activation of caspases including caspases 1 through 9; activation of NFκB; activation of the JNK and/or p38 kinase signaling cascades; inhibition of mitochondrial disruption and the activation of the mitochondrial permeability transition pore; activation of intracellular proteases such as the calpains. Examples of compounds that inhibit these apoptotic mechanisms include, but are not limited to, caspase inhibitors and inhibitors of the other enzymes mentioned above as mediators of apoptotic mechanisms.

Cells in the CNS are highly dependent on cell-to-cell interactions and interaction with the extracellular matrix for survival and proper function. However, during ischemic, hypoxic, or traumatic CNS insult these interactions are often disrupted and this can lead directly to or contribute to cellular dysfunction and death. Thus, therapies that maintain cell-to-cell and cell-to-extracellular matrix interaction during ischemic, hypoxic or traumatic CNS insult are expected to reduce dysfunction and cell death. Furthermore, the beneficial effects of therapies that maintain cell-to-cell and cell-to-extracellular matrix interaction during ischemic, hypoxic or traumatic CNS injury may be additive or synergistic with the benefits of inhibiting NR2B subunit containing NMDA receptors with a NR2B subunit selective NMDA receptor antagonist. Mechanisms that contribute to the disruption of cell-to-cell and cell-to-extracellular matrix interaction during ischemic, hypoxic or traumatic CNS insult include, but are not limited to, the activation of proteases which degrade the extracellular matrix. These include, but are not limited to, matrix metalloproteases such as MMP 1 through 13. Examples of compounds that inhibit these enzymes include, but are not limited to those referred to in the following patents and patent applications: U.S. Pat. No. 5,861,510, issued Jan. 19, 1999; European Patent Application EP 606,046, published Jul. 13, 1994; European Patent Application EP 935,963, published Aug. 18, 1999; PCT Patent Application WO 98/34918, published Aug. 13, 1998; PCT Patent Applications WO 98/08825 and WO 98/08815, both published Mar. 5, 1998; PCT Patent Application WO 98/03516, published Jan. 29, 1998; and PCT Patent Application WO 98/33768, published Aug. 6, 1998. The foregoing patents and patent applications are incorporated herein by reference in their entireties.

CNS ischemia, hypoxia, or trauma leads to an inflammatory response mediated by various components of the innate and adaptive immune system. Because of the nature of the CNS and its unique relationship to the immune system, the immune system activation caused by CNS ischemia, hypoxia, or trauma can exacerbate cellular dysfunction and death. The mechanisms whereby immune activation exacerbates CNS injury are many-fold. Immune cells resident to the CNS, such as astrocytes and microglia, are activated following CNS injury. Furthermore, peripheral immune cells are recruited to enter the CNS and also become activated. These cells include monocytes/macrophages, neutrophils, and T lymphopcytes. Recruitment and activation of these peripheral immune cells into the CNS after injury involves many of the same mechanisms by which these cells are recruited to and activated by injured tissue outside the CNS. The cell within the area of tissue injury and the vasculature around the site of injury begins to elaborate proteins that signal to immune cells circulating in the blood stream. These cells then adhere to the vascular epithelium and enter the area in and around the damaged tissue. These activated immune cells then promote many of the deleterious events listed above, including release of a variety of toxins and disruption of cell-to-cell and cell-to-extracellular matrix interactions.

Thus, inhibition of immune cell recruitment, adherence to the vasculature, activation, and formation and release of toxins and proteases in response to CNS ischemia, hypoxia, or trauma is hypothesized to reduce the cellular dysfunction and death caused by these CNS insults. The beneficial effects of inhibiting immune cell recruitment, activation, and formation and release of toxins and proteases during ischemic, hypoxic or traumatic CNS injury may be additive or synergistic with the benefits of inhibiting NR2B subunit containing NMDA receptors with a NR2B subunit selective NMDA receptor antagonist. Compounds that inhibit immune cell recruitment include, but are not limited to, antagonists to a wide variety of cytokine and chemokine receptors. Compounds that inhibit immune cell adherence to the vasculature include, but are not limited to, antibodies to a variety of cell adhesion molecules. Compounds that inhibit immune cell activation include, but are not limited to, antagonists to a wide variety of cytokine and chemokine receptors, and antibodies to a variety of cell adhesion molecules, antagonists of intracellular enzymes involved in transducing the activating signal into a cellular response such as antagonists of COX and COX2, various protein ser/thr and tyr kinases and intracellular proteases. Recruitment, adherence, and activation of CNS resident and peripheral immune cells can also be inhibited by the activation of cell signaling pathways that oppose this activation. Compounds that activate such signaling pathways include, but are not limited to, PPARγ activators.

In the case of thrombotic or embolic stroke, it has been observed that administration of agents that degrade thrombi and emboli can have a beneficial effect on patient survival, recovery and/or function. The mechanism of action of these agents is to promote the reperfusion of ischemic tissue. It is suggested here that the beneficial effects of agents that promote reperfusion following thrombotic or embolic stroke may be additive or synergistic with the benefits of inhibiting NR2B subunit containing NMDA receptors with a NR2B subunit selective NMDA receptor antagonist in these conditions. Compounds that promote reperfusion following thrombotic or embolic stroke include, but are not limited to, TPA, urokinase and streptokinase.

SUMMARY OF THE INVENTION

This invention relates to a method of treating hypoxic or ischemic stroke in a mammal, including a human, comprising administering to said mammal:

(a) a thrombolytic agent or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating hypoxic or ischemic stroke in a mammal, including a human, comprising:

(a) a thrombolytic agent or a pharmaceutically acceptable salt thereof;

(b) an NR2B subtype selective NMDA receptor antagonizing compound or a pharmaceutically acceptable salt thereof; and c) a pharmaceutically acceptable carrier;

wherein the active agents "a" and "b" are present in such composition in amounts that render the combination of the two agents effective in treating such disorder.

The term "treating", as used herein, refers to retarding or reversing the progress of, or alleviating or preventing either the disorder or condition to which the term "treating" applies, or one or more symptoms of such disorder or condition. The term "treatment", as used herein, refers to the act of treating a disorder or condition, as the term "treating" is defined above.

Preferred methods and pharmaceutical compositions of this invention include the above described methods and pharmaceutical compositions wherein the NMDA receptor antagonist is an NR2B subtype selective NMDA receptor antagonist of the formula

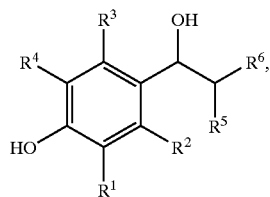

or a pharmaceutically acceptable acid addition salt thereof, wherein:

(a) $R^2$ and $R^5$ are taken separately and $R^1$, $R^2$, $R^3$ and $R^4$ are each independently hydrogen, $(C_1-C_6)$ alkyl, halo, $CF_3$, OH or $OR^7$ and $R^5$ is methyl or ethyl; or (b) $R^2$ and $R^5$ are taken together and are

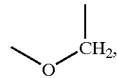

forming a chroman-4-ol ring, and $R^1$, $R^3$ and $R^4$ are each independently hydrogen, $(C_1-C_6)$ alkyl, halo, $CF_3$, OH or $OR^7$;

$R^6$ is

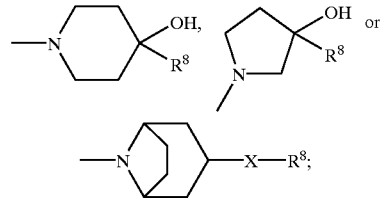

$R^7$ is methyl, ethyl, isopropyl or n-propyl;

$R^8$ is phenyl optionally substituted with up to three substituents independently selected from $(C_1-C_6)$ alkyl, halo and $CF_3$;

X is O, S or $(CH_2)n$; and n is 0, 1, 2, or 3.

Compounds of formula I are described in U.S. Pat. Nos. 5,185,343; 5,272,160; 5,338,754; 5,356,905; and 6,046,213 (which issued, respectively, on Feb. 9, 1993, Dec. 21, 1993, Aug. 16, 1994, Oct. 18, 1994, and Apr. 4, 2000); U.S. patent applications Ser. Nos. 08/292,651 (filed Aug. 18, 1994), 08/189,479 (filed Jan. 31, 1994) and 09/011,426 (filed Jun. 20, 1996); PCT International Application No. PCT/IB95/00398, which designates the United States (filed May 26, 1995) (corresponding to WO 96/37222); and PCT International Application No. PCT/IB95/00380, which designates the United States (filed May 18, 1995) (corresponding to WO 96/06081). All of the foregoing patents, United States patent applications and PCT international application are herein incorporated by reference in their entirety.

Preferred compounds for use in the methods and pharmaceutical compositions of the present invention include those of formula I wherein $R^2$ and $R^5$ are taken separately; $R^2$ and $R^3$ are hydrogen; $R^6$ is

and $R^8$ is phenyl, 4-halophenyl or 4-trifluoromethylphenyl. Within this group, more specific preferred compounds are those wherein $R^5$ is methyl having a 1S*,2S* relative stereochemistry:

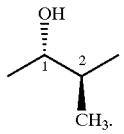

Other preferred compounds for use in the methods and pharmaceutical compositions of the present invention include those of formula I wherein $R^2$ and $R^5$ are taken together and are

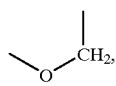

forming a chroman-4-ol ring. Within this group, preferred compounds also include those wherein the C-3 and C-4 positions of said chroman-4-ol ring have a 3R*,4S* relative stereochemistry:

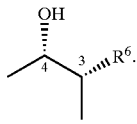

Within this group, preferred compounds also include those wherein $R^6$ is

and $R^8$ is phenyl or 4-halophenyl.

Compounds of formula I may contain chiral centers and therefore may exist in different enantiomeric and diastereomeric forms. This invention relates to the above methods of treatment using and the above pharmaceutical compositions comprising all optical isomers and all stereoisomers of compounds of the formula I and mixtures thereof.

The term "alkyl", as used herein, unless otherwise indicated, includes saturated monovalent hydrocarbon radicals having straight, branched or cyclic moieties or combinations thereof.

The term "one or more substituents", as used herein, refers to a number of substituents that equals from one to the maximum number of substituents possible based on the number of available bonding sites.

The terms "halo" and "halogen", as used herein, unless otherwise indicated, include chloro, fluoro, bromo and iodo.

Formula I above includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

NMDA receptor antagonists of the formula I that are particularly preferred for use in the methods and pharmaceutical compositions of this invention are the following: (+)-(1S, 2S)-1-(4-hydroxy-phenyl)-2-(4-hydroxy-4-phenylpiperidino)-1-yl)-1-propanol; (1S,2S)-1-(4-hydroxy-3-methoxyphenyl)-2-(4-hydroxy4-phenylpiperidino)-1-propanol; (1S,2S)-1-(4-hydroxy-3-methyl phenyl)-2-hydroxy-4-phenyl (piperidino)-1-propanol and (3R,4S)-3-(4-(4-fluorophenyl)-4-hydroxypiperidin-1-yl)-chroman-4,7-diol.

Examples of suitable thrombolytic agents that can be employed in the methods and pharmaceutical compositions of this invention, as described above, are prourokinase, streptokinase, and tissue plasminogen activator (TPA), Other examples of suitable thrombolytic agents that can be employed in the methods and pharmaceutical compositions of this invention are the following proteins, which can be obtained by making changes to TPA as described in U.S. Pat. No. 5,976,530, which issued on Nov. 2, 1999: (a) TPA having lysine 277 substituted with another amino acid and further comprising a deletion of from 3 to 25 amino acids from the C-terminus; and (b) TPA having lysine 277 substituted with another amino acid, and further comprising a deletion of from 3 to 25 amino acids from the C-terminus, and further comprising a substitution of at least one of asparagine 117, asparagine 184 and asparagine 448 with another amino acid.

Tissue plasminogen activator (TPA), a protein (serine protease) capable of dissolving blood clots, is described in detail in U.S. Pat. No. 5,112,609, which issued on May 12, 1992. This patent is incorporated herein by reference in its entirety. TPA can be obtained from a normal or neoplastic cell line of the kind described in Biochimica et Biophysica Acta., 1979, 580, 140–153, and European Patent Publications EP-A-41766 and EP-A-113319. TPA can also be obtained from a cultured transformed or transfected cell line derived using recombinant DNA technology as described in, for example, European Patent Publications EP-A-93619, EP-A-117059 and EP-A-117060. U.S. Pat. No. 5,976,530, which issued on Nov. 2, 1999. The recombinant enzyme Altepase is a tissue plasminogen activator produced by recombinant DNA technology.

This invention also relates to a method of treating traumatic brain injury or hypoxic or ischemic stroke in a mammal, including a human, comprising administering to said mammal:

(a) a glycine site antagonizing compound (e.g., gavestinil) or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) a glycine site antagonizing compound (e.g., gavestinil) or a pharmaceutically acceptable salt thereof;

(b) an NR2B subtype selective NMDA receptor antagonizing compound or a pharmaceutically acceptable salt thereof; and render the combination of the two agents effective in treating such disorder.

Examples of glycine site antagonists that are suitable for use in the pharmaceutical compositions and methods of this invention are those referred to in the following: U.S. Pat. No. 5,942,540, which issued on Aug. 24, 1999; World Patent Application WO 99/34790 which issued on Jul. 15, 1999; WO 98/47878, which was published on Oct. 29, 1998; World Patent Application WO 98/42673, which was published on Oct. 1, 1998; European Patent Application EP 966475A1, which was published on Dec. 29, 1991; World Patent Application 98/39327, which was published on Sep. 11, 1998; World Patent Application WO 98104556, which was published on Feb. 5, 1998; World Patent Application WO 97/37652, which was published on Oct. 16, 1997; U.S. Pat. No. 5,837,705, which was issued on Oct. 9, 1996; World Patent Application WO 97/20553, which was published on Jun. 12, 1997; U.S. Pat. No. 5,886,018, which was issued on Mar. 23, 1999; U.S. Pat. No. 5,801,183, which was issued on Sep. 1, 1998; World Patent Application WO 95/07887, which was issued on Mar. 23, 1995; U.S. Pat. No. 5,686,461, which was issued on Nov. 11, 1997; U.S. Pat. No. 5,614,509, which was issued on Mar. 25, 1997; U.S. Pat. No. 5,510,367, which was issued on Apr. 23, 1996; European Patent Application 517,347A1, which was published on Dec. 9, 1992; U.S. Pat. No. 5,260,324, which published on Nov. 9, 1993. The foregoing patents and patent applications are incorporated herein by reference in their entireties.

Other examples of glycine site antagonists that can be used in the pharmaceutical composition and methods of this invention are N-(6,7-dichloro-2,3-dioxo-1,2,3,4-tetrahydro-quinoxalin-5-yl)N-(2-hydroxy-ethyl)-methanesulfonamide and 6,7-dichloro-5-[3-methoxymethyl-5-(1-oxy-pyridin-3-yl)-[1,2,4]triazol-4-yl]-1,4-dihydro-quinoxa-line-2,3-dione This invention also relates to a method of treating traumatic brain injury or hypoxic or ischemic stroke in a mammal, including a human, comprising administering to said mammal:

(a) a sodium channel blocking compound or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) a sodium channel blocking compound or a pharmaceutically acceptable salt thereof, (b) an NR2B subtype selective NMDA receptor antagonizing compound or a pharmaceutically acceptable salt thereof; and c) a pharmaceutically acceptable carrier;

wherein the active agents "a" and "b" are present in such composition in amounts that render the combination of the two agents effective in treating such disorder.

Examples of suitable sodium channel blocking compounds (i.e., sodium channel antagonists) that can be employed in the methods and pharmaceutical compositions of this invention, as described above, are ajmaline, procainamide, flecainide and riluzole.

This invention also relates to a method of treating traumatic brain injury or hypoxic or ischemic stroke in a mammal, including a human, comprising administering to said mammal:

(a) a calcium channel blocking compound or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) a calcium channel blocking compound or a pharmaceutically acceptable salt thereof;

(b) an NR2B subtype selective NMDA receptor antagonizing compound or a pharmaceutically acceptable salt thereof; and (c) a pharmaceutically acceptable carrier;

wherein the active agents "a" and "b" are present in such composition in amounts that render the combination of the two agents effective in treating such disorder.

Examples of suitable calcium channel blocking compounds (i.e., calcium channel antagonists) that can be employed in the methods and pharmaceutical compositions of this invention, as described above, are diltiazem, omega-conotoxin GVIA, methoxyverapamil, amlodipine, felodipine, lacidipine, and mibefradil.

This invention also relates to a method of treating traumatic brain injury or hypoxic or ischemic stroke in a mammal, including a human, comprising administering to said mammal:

(a) a potassium channel opening compound or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) a potassium channel opening compound or a pharmaceutically acceptable salt thereof, (b) an NR2B subtype selective NMDA receptor antagonizing compound or a pharmaceutically acceptable salt thereof; and (c) a pharmaceutically acceptable carrier;

wherein the active agents "a" and "b" are present in such composition in amounts that render the combination of the two agents effective in treating such disorder.

Examples of suitable potassium channel openers that can be employed in the methods and pharmaceutical compositions of this invention, as described above, are diazoxide, flupirtine, pinacidil, levcromakalim, rilmakalim, chromakalim, PCO-400 (J. Vasc. Res., November–December 1999, 36 (6), 516–23) and SKP-450 (2-[2"(1",3"-dioxolone)-2-methyl]-4-(2'-oxo-1'-pyrrolidinyl)-6-nitro-2H-1-benzopyran).

This invention also relates to a method of treating traumatic brain injury or hypoxic or ischemic stroke in a mammal, including a human, comprising administering to said mammal:

(a) an antiinflammatory compound or a pharmaceutically acceptable salt thereof; and (b) an NR2B subtype selective NMDA receptor antagonizing compound or a pharmaceutically acceptable salt thereof; wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) an antiinflammatory compound or a pharmaceutically acceptable salt thereof;

(b) an NR2B subtype selective NMDA receptor antagonizing compound or a pharmaceutically acceptable salt thereof; and c) a pharmaceutically acceptable carrier;

wherein the active agents "a" and "b" are present in such composition in amounts that render the combination of the two agents effective in treating such disorder.

Examples of suitable antiinflammatory compounds that can be employed in the methods and pharmaceutical compositions of this invention, as described above, are NSAIDs, COXII inhibitors, acetominophen and steroidal antiinflammatory agents such as methyl prednilolone and cortisone. Examples of nonsteroidal antiinflamatory drugs (NSAIDs) are diclofenac sodium, nabumetone, naproxen, naproxen sodium, ketorolac, ibuprofen and indomethacin.

Examples of suitable COXII inhibitors that can be employed in the methods and pharmaceutical compositions of this invention are those referred to in the following: U.S. Provisional Patent Application 60/134,311, which was filed on May 14, 1999; U.S. Provisional Patent Application 60/134,312, which was filed on May 14, 1999; U.S. Provisional Patent Application 60/134,309, which was filed on May 14, 1999. The foregoing applications are incorporated herein by reference in their entireties.

Other examples of suitable COXII inhibitors that can be employed in the methods and pharmaceutical compositions of this invention are those referred to in the following: U.S. Pat. No. 5,817,700, issued Oct. 6, 1998; World Patent Application WO97/28121, published Aug. 7, 1997; U.S. Pat. No. 5,767,291, issued Jun. 16, 1998; U.S. Pat. No. 5,436,265, issued Jul. 25 1995; U.S. Pat. No. 5,474,995, issued Dec. 12, 1995; U.S. Pat. No. 5,536,752, issued Jul. 16, 1996; U.S. Pat. No. 5,550,142, issued Aug. 27, 1996; U.S. Pat. No. 5,604,260, issued Feb. 18, 1997; U.S. Pat. No. 5,698,584, issued Dec. 16, 1997; U.S. Pat. No. 5,710,140, issued Jan. 20, 1998; U.S. Pat. No. 5,840,746, issued Nov. 24, 1998; Great Britain Patent Application 986430, filed Mar. 25, 1998; World Patent Application WO97/28120, published Aug. 7, 1997; Great Britain Patent Application 9800689, filed Jan. 14, 1998; Great Britain Patent Application 9800688, filed Jan. 14, 1998; World Patent Application WO94/14977, published Jul. 7, 1994; World Patent Application WO98/43966, published Oct. 8, 1998; World Patent Application WO98/03484, published Jan. 29, 1998; World Patent Application WO98/41516, published Sep. 24, 1998; World Patent Application WO98/41511, published Sep. 24, 1998; Great Britain Patent Application 2,319,032, issued May 13, 1998; World Patent Application WO96/37467, published Nov. 28, 1996; World Patent Application WO96/37469, published Nov. 28,1996; World Patent Application WO96/36623, published Nov. 21, 1996; World Patent Application WO98/00416, published Jan. 8, 1998; World Patent Application WO97/44027, published Nov. 27, 1997; World Patent Application WO97/44028, published Nov. 27, 1997; World Patent Application WO96/23786, published Aug. 8, 1996; World Patent Application WO97/40012, published Oct. 30, 1997; World Patent Application WO96/19469, published Jun. 27, 1996; World Patent Application WO97/36863, published Oct. 9, 1997; World Patent Application WO97/14691, published Apr. 24, 1997; World Patent Application WO97/11701, published Apr. 3, 1997; World Patent Application WO96/13483, published May 9, 1996; World Patent Application WO96/37468, published Nov. 28, 1996; World Patent Application WO96/06840, published Mar. 7, 1996; World Patent Application WO94/26731, published Nov. 24, 1994; World Patent Application WO94/20480, published Sep. 15, 1994; U.S. Pat. No. 5,006,549, issued Apr. 9, 1991; U.S. Pat. No. 4,800,211, issued Jan. 24, 1989; U.S. Pat. No. 4,782,080, issued Nov. 1, 1988; U.S. Pat. No. 4,720,503, issued Jan. 19, 1988; U.S. Pat. No. 4,760,086, issued Jul. 26,1988; U.S. Pat. No. 5,068,248, issued Nov. 26, 1991; U.S. Pat. No. 5,859,257, issued Jan. 12, 1999; World Patent Application WO98/47509, published Oct. 29, 1998; World Patent Application WO98/47890, published Oct. 29, 1998; World Patent Application WO98/43648, published Oct. 8, 1998; World Patent Application WO98/25896, published Jun. 18,1998; World Patent Application WO98/22101, published May 28, 1998; World Patent Application WO98/16227, published Apr. 23, 1998; World Patent Application WO98/06708, published Feb. 19, 1998; World Patent Application WO97/38986, published Oct. 23, 1997; U.S. Pat. No. 5,663,180, issued Sep. 2, 1997; World Patent Application WO97/29776, published Aug. 21,1997; World Patent Application WO97/29775, published Aug. 21, 1997; World Patent Application WO97/29774, published Aug. 21,1997; World Patent Application WO97/27181, published Jul. 31, 1997; World Patent Application WO95/11883, published May 4, 1995; World Patent Application WO97/14679, published Apr. 24, 1997; World Patent Application WO97/11704, published Apr. 3,1997; World Patent Application WO96/41645, published Dec. 27, 1996; World Patent Application WO96/41626, published Dec. 27, 1996; World Patent Application WO96/41625, published Dec. 27,1996; World Patent Application WO96/38442, published Dec. 5,1996; World Patent Application WO96/38418, published Dec. 5, 1996; World Patent Application WO96/36617, published Nov. 21, 1996; World Patent Application WO96/24585, published Aug. 15, 1996; World Patent Application WO96/24584, published Aug. 15, 1996; World Patent Application WO96/16934, published Jun. 6, 1996; World Patent Application WO96/03385, published Feb. 8, 1996; World Patent Application WO96/12703, published May 2, 1996; World Patent Application WO96/09304, published Mar. 28, 1996; World Patent Application WO96/09293, published Mar. 28, 1996; World Patent Application WO96/03392, published Feb. 8, 1996; World Patent Application WO96/03388, published Feb. 8, 1996; World Patent Application WO96/03387, published Feb. 8, 1996; World Patent Application WO96/02515, published Feb. 1, 1996; World Patent Application WO96/02486, published Feb. 1, 1996; U.S. Pat. No. 5,476,944, issued Dec. 19, 1995; World Patent Application WO95/30652, published Nov. 16, 1995; U.S. Pat. No. 5,451,604, published Sep. 19, 1995; World Patent Application WO95/21817, published Aug. 17, 1995; World Patent Application WO95/21197, published Aug. 10, 1995; World Patent Application WO95/15315, published Jun. 8, 1995; U.S. Pat. No. 5,504, 215, issued Apr. 2, 1996; U.S. Pat. No. 5,508,426, issued Apr. 16, 1996; U.S. Pat. No. 5,516,907, issued May 14, 1996; U.S. Pat. No. 5,521,207, issued May 28, 1998; U.S. Pat. No. 5,753,688, issued May 19, 1998; U.S. Pat. No. 5,760,068, issued Jun. 2, 1998; U.S. Pat. No. 5,420,343, issued May 30, 1995; World Patent Application WO95/30656, published Nov. 16, 1995; U.S. Pat. No. 5,393,790, issued Feb. 28, 1995; and World Patent Application WO94/27980, published Feb. 8, 1994. The foregoing patents and patent applications are incorporated herein by reference in their entireties.

This invention also relates to a method of treating traumatic brain injury or hypoxic or ischemic stroke in a mammal, including a human, comprising administering to said mammal:

(a) a GABA-A receptor modulator (e.g., a GABA-A receptor agonist) or a pharmaceutically acceptable salt thereof; and (b) an NR2B subtype selective NMDA receptor antagonizing compound or a pharmaceutically acceptable salt thereof; wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) a GABA-A receptor modulator (e.g., a GABA-A receptor agonist) or a pharmaceutically acceptable salt thereof;

(b) an NR2B subtype selective NMDA receptor antagonizing compound or a pharmaceutically acceptable salt thereof; and c) a pharmaceutically acceptable carrier;

wherein the active agents "a" and "b" are present in such composition in amounts that render the combination of the two agents effective in treating such disorder.

Examples of suitable GABA-A receptor modulators that can be employed in the methods and pharmaceutical compositions of this invention, as described above, are clomethiazole, and. Other examples of GABA-A modulators that can be used in the pharmaceutical compositions and methods of this invention are those that are referred to in the following: World Patent Application WO 99/25353, which was published on May 27, 1999; World Patent Application WO 96/25948, which was published on Aug. 29, 1996; World Patent Application WO 99137303, which was published on Jul. 29, 1999; U.S. Pat. No. 5,925,770, which was issued on Jul. 20, 1999; U.S. Pat. No. 5,216,159, which was issued on Jun. 1, 1993; U.S. Pat. No. 5,130,430, which was issued on Jul. 14, 1992; U.S. Pat. No. 5,925,770, which was issued on Jul. 20, 1999; and World Patent Application WO 99/10347, which was published on Mar. 4, 1999.

This invention also relates to a method of treating traumatic brain injury or hypoxic or ischemic stroke in a mammal, including a human, comprising administering to said mammal:

(a) an antioxidant compound (e.g., alpha-tocopherol) or a pharmaceutically acceptable salt thereof; and (b) an NR2B subtype selective NMDA receptor antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) an antioxidant compound (e.g., alpha-tocopherol) or a pharmaceutically acceptable salt thereof;

(b) an NR2B subtype selective NMDA receptor antagonizing compound or a pharmaceutically acceptable salt thereof; and (c) a pharmaceutically acceptable carrier;

wherein the active agents "a" and "b" are present in such composition in amounts that render the combination of the two agents effective in treating such disorder.

Examples of suitable antioxidant compounds that can be employed in the methods and pharmaceutical compositions of this invention, as described above, are vitamin E, vitamin A, calcium dobesilate, stobadine, alpha-tocopherol, ascorbic acid, alpha-lipoic acid, corcumin, catalase, prevastatin, N-acetylcysteine, nordihydroguaiaretic acid, pyrrolidine dithiocarbamate, LY341122, and Metexyl (4-methoxy-2,2, 6,6-tetramethylpiperidine-1-oxyl).

This invention also relates to a method of treating traumatic brain injury or hypoxic or ischemic stroke in a mammal, including a human, comprising administering to said mammal:

(a) an AMPA/kainate receptor antagonizing compound or a pharmaceutically acceptable salt thereof; and (b) an NR2B subtype selective NMDA antagonizing compound or a pharmaceutically acceptable salt thereof;

wherein the active agents "a" and "b" above are present in amounts that render the combination of the two agents effective in treating hypoxic or ischemic stroke.

This invention also relates to a pharmaceutical composition for treating traumatic brain injury or hypoxic or ischemic stroke in a mammal, including a human, comprising:

(a) an AMPA/kainate receptor antagonizing compound or a pharmaceutically acceptable salt thereof;

(b) an NR2B subtype selective NMDA antagonizing compound or a pharmaceutically acceptable salt thereof; and (c) a pharmaceutically acceptable carrier;

wherein the active agents "a" and "b" are present in such composition in amounts that render the combination of the two agents effective in treating such disorder.

Examples of suitable AMPA/kainate receptor antagonizing compounds that can be employed in the methods and pharmaceutical compositions of this invention, as described above, are 6-cyano-7-nitroquinoxalin-2,3-dione (CNQX), 6-nitro-7-sulphamoylbenzo[f]quinoxaline-2,3-dione (NBQX), 6,7-dinitroquinoxaline-2,3-dione (DNQX), 1-(4-aminophenyl)-4-methyl-7,8-methylenedioxy-5H-2,3-benzodiazepine hydrochloride and 2,3-dihydroxy-6-nitro-7-sulfamoylbenzo-[f]quinoxaline.

This invention also relates to a method of treating hypoxic or ischemic stroke in a mammal, including a human, comprising administering to said mammal:

(a) a NOS inhibiting compound or a pharmaceutically acceptable salt thereof; and (b) an NR2B subtype selective NMDA antagonizing compound or a pharmaceutically acceptable salt thereof; wherein the active agents "a" and "b" above are present in amounts that render the combination of the two agents effective in treating hypoxic or ischemic stroke.

This invention also relates to a pharmaceutical composition for treating hypoxic or ischemic stroke in a mammal, including a human, comprising:

(a) a NOS inhibiting compound or a pharmaceutically acceptable salt thereof;

(b) an NR2B subtype selective NMDA antagonizing compound or a pharmaceutically acceptable salt thereof; and (c) a pharmaceutically acceptable carrier;

wherein the active agents "a" and "b" are present in such composition in amounts that render the combination of the two agents effective in treating such disorder.

There are three known isoforms of NOS—an inducible form (I-NOS) and two constitutive forms referred to as, respectively, neuronal NOS (N-NOS) and endothelial NOS (E-NOS). Each of these enzymes carries out the conversion of arginine to citrulline while producing a molecule of nitric oxide (NO) in response to various stimuli. It is believed that excess nitric oxide (NO) production by NOS plays a role in the pathology of a number of disorders and conditions in mammals. For example, NO produced by I-NOS is thought to play a role in diseases that involve systemic hypotension such as toxic shock and therapy with certain cytokines. It has been shown that cancer patients treated with cytokines such as interleukin 1 (IL-1), interleukin 2 (IL-2) or tumor necrosis factor (TNF) suffer cytokine-induced shock and hypotension due to NO produced from macrophages, ie. inducible NOS (I-NOS), see *Chemical & Engineering News*, Dec. 20, p. 33, (1993). I-NOS inhibitors can reverse this. It is also believed that I-NOS plays a role in the pathology of diseases of the central nervous system such as ischemia. For example, inhibition of I-NOS has been shown to ameliorate cerebral ischemic damage in rats, see Am. *J. Physiol.*, 268, p. R286 (1995)). Suppression of adjuvant induced arthritis by selective inhibition of I-NOS is reported in Eur. *J. Pharmacol.*, 273, p. 15–24 (1995).

NO produced by N-NOS is thought to play a role in diseases such as cerebral ischemia, pain, and opiate tolerance. For example, inhibition of N-NOS decreases infarct volume after proximal middle cerebral artery occlusion in the rat, see *J. Cerebr. Blood Flow Metab.*, 14, p. 924–929 (1994). N-NOS inhibition has also been shown to be effective in antinociception, as evidenced by activity in the late phase of the formalin-induced hindpaw licking and acetic acid-induced abdominal constriction assays, see Br. *J. Pharmacol.*, 110, p. 219–224 (1993). In addition, subcutaneous injection of Freund's adjuvant in the rat induces an increase in NOS-positive neurons in the spinal cord that is manifested in increased sensitivity to pain, which can be treated with NOS inhibitors, see *Japanese Journal of Pharmacology*, 75, p. 327–335 (1997). Finally, opioid withdrawal in rodents has been reported to be reduced by N-NOS inhibition, see *Neuropsychopharmacol.*, 13, p. 269–293 (1995).

Examples of NOS inhibiting compounds that can be used in the methods and pharmaceutical compositions of the present invention are those referred to in: U.S. provisional application 60/057094, which was filed Aug. 27, 1997 and is entitled "2-Aminopyrindines Containing Fused Ring Substituents"; the PCT application having the same title that was filed on May 5, 1998, which designates the United States and claims priority from provisional application 60/057094; PCT patent application WO 97/36871, which designates the United States and was published on Oct. 9, 1997; U.S. provisional patent application 60/057739 of John A. Lowe, III, entitled "6-Phenylpyridin-2-yl-amine Derivatives", which was filed on Aug. 28, 1997; PCT patent application PCT/IB98/00112, entitled "4-Amino-6-(2-substituted-4-phenoxy)-substituted-pyridines", which designates the United States and was filed on Jan. 29, 1998; PCT patent application PCT/IB97/01446, entitled "6-Phenylpyridyl-2-amine Derivatives", which designates the United States and was filed on Nov. 17, 1997; and the U.S. provisional application of John A. Lowe, III, that was filed on Jun. 3, 1998 and is entitled "2-Aminopyridines Containing Fused Ring Substituents". The foregoing patent applications are incorporated herein by reference in their entirety.

DETAILED DESCRIPTION OF THE INVENTION

The NR2B subtype selective NMDA antagonists of formula I are readily prepared. The compounds of formula I wherein $R^2$ and $R^5$ are taken together forming a chroman-4-ol ring and $R^1$, $R^3$, and $R^4$ are hydrogen, can be prepared by one or more of the synthetic methods described in U.S. Pat. No. 5,356,905, referred to above. The compounds of formula I wherein $R^2$ and $R^5$ are taken separately and $R^1$, $R^2$, $R^3$ and $R^4$ are hydrogen can be prepared by one or more of the synthetic methods described in U.S. Pat. Nos. 5,185,343, 5,272,160, and 5,338,754, all of which are referred to above. The compounds of formula I can also be prepared by one or more of the synthetic methods described in U.S. patent application Ser. Nos. 08/292,651, 08/189,479 and 09/011,426; PCT International Application No. PCT/IB95/00398, which designates the United States (filed May 26, 1995) (corresponding to WO96/37222); and PCT Application No. PCT/IB95/00380, which designates the United States (filed May 18, 1995) (corresponding to WO 96/06081), all of which are referred to above.

A preferred compound, (1S,2S)-1-(4-hydroxyphenyl)-2-(4-hydroxy-4-phenylpiperidin-1-yl)-1-propanol ((1S,2S) free base), and its tartrate salt, can be prepared as described in U.S. Pat. No. 5,272,160, referred to above. The resolution of racemic 1-(4-hydroxyphenyl)-2-(4-hydroxy-4-phenylpiperidin-1-yl)-1-propanol to form the (1S,2S) free base and the corresponding (1R,2R) enantiomer can be carried out as described in U.S. patent application No. 09/011,426, referred to above, and as exemplified in Example 1 below.

The anhydrous mesylate of the (1S,2S) free base can be prepared as described in U.S. Pat. No. 5,272,160, referred to above. The anhydrous mesylate of the (1S,2S) free base, when equilibrated in an 81% relative humidity environment, will convert to the mesylate salt trihydrate of the (1S,2S) enantiomer.

The mesylate salt trihydrate of (1S,2S)-1-(4-hydroxyphenyl)-2-(4-hydroxy-4-phenylpiperidin-1-yl)-1-propanol can be prepared from the (1S,2S) free base as described in United States provisional patent application entitled "(1S,2S)-1-(4-Hydroxyphenyl)-2-(4-Hydroxy-4-Phenylpiperidin-1-yl)-1-Propanol Methanesulfonate Trihydrate", referred to above. In this method, (1S,2S) free base is dissolved in water at 30° C. To this solution is added at least 1 equivalent of methane sulfonic acid and the resulting mixture is warmed to 60–65° C. The warm solution can be filtered to render it particulate free. The solution is concentrated to approximately 40% of the initial volume, cooled below 10° C., isolated by filtration and dried to a water content (measured Karl Fischer titration) of approximately 11.3%. The resulting crystalline mesylate salt trihydrate can be further purified by recrystallization.

Another preferred compound, (3R,4S)-3-[4-(4-fluorophenyl)4-hydroxy-piperidin-1-yl]-chroman-4,7-diol ((3R,4S) chromanol), can be prepared as described in U.S. Pat. No. 5,356,905, U.S. patent application Ser. No. 08/189,479, and United States provisional patent application entitled "Process For The Resolution of Cis-Racemic 7-Benzyloxy-3-[4-(4-Fluorophenyl)-4-Hydroxy-Piperidin-1-yl]-Chroman4-ol Dibenzoyl-D-Tartrate", all three of which are referred to above. The starting materials and reagents required for the synthesis of the (3R,4S) chromanol are readily available, either commercially, according to synthetic methods disclosed in the literature, or by synthetic methods exemplified in the description provided below.

The (3R,4S) chromanol can be prepared by fractional crystallization of the L-proline ester of racemic cis-7-benzyloxy-3-[4-(4-fluorophenyl)-4-hydroxy-piperidin-1-yl]-chroman-4-ol, as described in U.S. pat. application Ser. No. 08/189,479, referred to above. In a preferred method, the resolution method described in United States provisional patent application entitled "Process For The Resolution Of Cis-Racemic 7-Benzyloxy-3-[4-(4-Fluorophenyl)-4-Hydroxy-Piperidin-1-yl]-Chroman-4-ol Dibenzoyl-D-Tartrate", referred to above, and as exemplified in Example 3. In this method, the parent chromanol is prepared by dissolving racemic cis-7-benzyloxy-3-[4-(4-fluorophenyl)4-hydroxy-piperidin-1-yl]-chroman4-ol with an equal molar amount of dibenzoyl-D-tartaric acid in boiling aqueous ethanol. Racemic cis-7-benzyloxy-3-[4-(4-fluorophenyl)4- hydroxy-piperidin-1-yl]-chroman-4-ol is prepared as described in U.S. patent application Ser. No. 08/189,479, referred to above. The concentration of aqueous ethanol is not critical and may be varied between 75% and 95% ethanol (ETOH). A concentration of 9:1/ETOH:$H_2O$ has been found to be effective and is preferred. A sufficient amount of the aqueous ethanol solvent to dissolve the racemic compound is required. This amount has been found to be about 17 ml per gram of racemic compound.

Upon stirring while heating under reflux, the racemic compound dissolves to form a hazy solution which is allowed to cool with stirring whereupon the (+) isomer, (3R,4S)-7-benzyloxy-3-[4-(4-fluorophenyl)-4-hydroxy-piperidin-yl]-chroman-4-ol dibenzoyl-D-tartrate, precipitates and may be collected by filtration and washed with aqueous ethanol. This is the tartrate salt of the (3R,4S) chromanol. The lactate and mandelate salts of the (3R,4S) chromanol are prepared in an analogous manner. This initial product is of about 90% optical purity. If a higher purity is desired, the product may be heated again with aqueous ethanol, cooled and the product collected and washed. Two such treatments were found to yield the (+) isomer of 99.4% optical purity in an overall yield of 74%. This procedure is preferred over the procedure described in U.S. patent application Ser. No. 08/189,479, referred to above, in that it avoids a reduction step with lithium aluminum hydride and is therefore more suitable for bulk operations. This procedure also produces a significantly higher yield of the desired product.

The above described (+) isomer can be converted to (3R,43)-3-[4-(4-fluorophenyl)-4-hydroxy-piperidin-1-yl]-chroman-4,7-diol by standard procedures. For example, treatment with dilute base can be used to free the piperidinyl base and subsequent hydrogeneration removes the 7-benzyl group to yield the (3R,4S) chromanol.

In general, the pharmaceutically acceptable acid addition salts of the compounds of formula I can readily be prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

As indicated above, selectivity of compounds for the $NR^2B$-subunit containing NMDA receptor is defined as an affinity for the racemic [$^3H$](+)-(1S, 2S)-1-(4-hydroxyphenyl)-2-(4-hydroxy-4-phenylpiperidino)-1-propanol binding site in forebrain of rats, as described in Chenard and Menniti (Antagonists Selective for NMDA receptors containing the $NR^2B$ Subunit, *Current Pharmaceutical Design*, 1999, 5:381–404). This affinity is assessed in a radioligand binding assay as described below. Selective compounds are those which displace specific binding of racemic [$^3H$]CP-101,606 from rat forebrain membranes with an $IC_{50} \leq 5$ µM.

The binding of racemic [$^3H$] (+)-(1S, 2S)-1-(4-hydroxyphenyl)-2-(4-hydroxy-4-phenylpiperidino)-1-propanol to rat forebrain membranes is measured as described by Menniti et al. (CP-101,606, a potent neuroprotectant selective for forebrain neurons, *European Journal of Pharmacology*, 1997, 331:117–126). Forebrains of adult male CD rats are homogenized in 0.32M sucrose at 4° C. The crude nuclear pellet is removed by centrifugation at 1,000×g for 10 minutes, and the supernatant centrifuged at 17,000×g for 25 minutes. The resulting pellet is resuspended in 5 mM Tris acetate pH 7.4 at 4° C. for 10 minutes to lyse cellular particles and again centrifuged at 17,000×g. The resulting pellet is washed twice in Tris acetate, resuspended at 10 mg protein/ml and stored at −20° C. until use.

For binding assays, membranes are thawed, homogenized, and diluted to 0.5 mg protein/ml with 50 mM Tris HCl, pH 7.4. Compounds under study are added at various concentrations followed by racemic [$^3H$] (+)-(1S, 2S)-1-(4-hydroxy-phenyl)-2-(4-hydroxy-4-phenylpiperidino)-1-propanol (specific activity 42.8 Ci/mmol, 5 nM final concentration). Following incubation for 20 min at 30° C. in a shaking water bath, samples are filtered onto Whatman GFB glass fiber filters using a MB-48R Cell Harvester (Brandel Research and Development Laboratories, Gaithersburg Md.). Filters are washed for 10 s with ice cold Tris HCl buffer and the radioactivity trapped on the filter quantified by liquid scintillation spectroscopy. Nonspecific binding is determined in parallel incubations containing 100 µM racemic (+)-(1 S, 2S)-1-(4-hydroxy-phenyl)-2-(4-hydroxy-4-phenylpiperidino)-1-propanol. Specific binding is defined as total binding minus nonspecific binding.

Compounds of the formula I have selectivity for $NR^2B$ subunit-containing NMDA receptors over $\alpha_1$-adrengergic receptors. Affinity for the $NR^2B$ subunit containing NMDA receptor is measured as the $IC_{50}$ for displacement of specific binding of racemic [$^3H$] (+)-(1S, 2S)-1-(4-hydroxy-phenyl)-2-(4-hydroxy-4-phenylpiperidino)-1-propanol from rat forebrain membranes (described above). Affinity for the $\alpha_1$-adrengergic receptor is defined as the $IC_{50}$ for displacement of specific binding of racemic [$^3H$]prazosin from rat brain membranes, measured as described by Greengrass and Bremner (*Binding Characteristics of [3H]prazosin to Rat Brain α-Adrenergic Receptors, European Journal of Pharmacology*, 55, 323–326, (1979)). A compound with a ratio of ([$^3H$]prazosin/[$^3H$] (+)-(1S, 2S)-1-(4-hydroxy-phenyl)-2-(4-hydroxy-4-phenylpiperidino)-1-propanol) affinity greater than three is considered selective.

Forebrains of adult male Sprague Dawley rats are homogenized in 20 volumes of ice cold 50 mM Tris/HCl buffer (pH 7.7). The homogenate is centrifuged at 50,000×g for 10 minutes at 4° C. The pellet is resuspended and centrifuged under identical conditions and the final pellet is resuspended in 80 volumes of 50 mM Tris/HCl (pH 8.0) at 4° C.

For binding assays, compounds under study are added at various concentrations to 500 µg membrane protein in 1 ml of 50 mM Tris/HCl buffer, followed by [$^3H$]prazosin (Amersham, specific activity 33 Ci/mmol, 0.2 nM final concentration). Following incubation for 30 min at 25° C. in a shaking water bath, samples are filtered onto Whatman GFB glass fiber filters using a MB-48R Cell Harvester (Brandel Research and Development Laboratories, Gaithersburg Md.). Filters are washed three times for 10 s with ice cold Tris HCl buffer and the radioactivity trapped on the filter quantified by liquid scintillation spectroscopy. Nonspecific binding is determined in parallel incubations containing 100 nM prazosin. Specific binding is defined as total binding minus nonspecific binding.

NR2B selective NMDA receptor antagonists useful in the practice of the invention may also be used in the form of a pharmaceutically acceptable salt. The expression "pharmaceutically-acceptable acid addition salts" is intended to include but not be limited to such salts as the hydrochloride, hydrobromide, sulfate, hydrogen sulfate, phosphate, hydrogen phosphate, dihydrogenphosphate, acetate, succinate, citrate, tartrate, lactate, mandelate, methanesulfonate (mesylate) and p-toluenesulfonate (tosylate) salts. The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

NMDA receptor antagonists, and, in particular, NR2B selective NMDA receptor antagonists, can also be administered in combination with a selective serotonin reuptake inhibitor (SSRI). Examples of selective serotonin reuptake inhibitors that can be administered, either as part of the same pharmaceutical composition or in a separate pharmaceutical composition, with an NR2B selective NMDA receptor antagonist, include: fluoxetine, fluvoxamine, paroxetine and sertraline, and pharmaceutically acceptable salts thereof.

This invention relates both to methods of treatment in which the NMDA antagonist and the other active ingredient in the claimed combinations are administered together, as part of the same pharmaceutical composition, as well as to methods in which the two active agents are administered separately, as part of an appropriate dose regimen designed to obtain the benefits of the combination therapy. The appropriate dose regimen, the amount of each dose administered, and the intervals between doses of the active agents will depend upon the particular NMDA antagonist and other active ingredient being used in combination, the type of pharmaceutical formulation being used, the characteristics of the subject being treated and the severity of the disorder being treated.

Generally, in carrying out the methods of this invention, COX-2 inhibitors will administered to an average adult human in amounts ranging from about 5 to about 300 mg per day, depending on the COX-2 inhibitor, severity of the headache and the route of administration. NSAIDS, in carrying out the methods of this invention, will generally be administered to an average adult human in amounts ranging from about 7 to about 2,000 mg per day. NMDA receptor antagonists, including glycine site antagonists, in carrying out the methods of this invention, will generally be administered to an average adult human in amounts ranging from about 25 to about 1500 mg per day.

Thrombolytic agents, in carrying out the methods of this invention, will generally be administered to an average adult human in amounts ranging from about 7000 to about 36,000 IU per kg body weight per day.

Calcium channel antagonists, potassium channel openers, sodium channel antagonists, and antioxidants, in carrying out the methods of this invention, will generally be administered to an average adult human in amounts within the ranges used when such agents are administered, respectively, as single active pharmaceutical agents. Such dosages are available in the scientific and medical literature, and, for substances that have been approved for human use by the Food and Drug Administration, in the current edition (presently the $53^{rd}$ edition) of the Physician's Desk Reference, Medical Economics Company, Montvale, N.J.

In some instances, dosage levels below the lower limit of the aforesaid range may be more than adequate, while in other cases still larger doses may be employed without causing any harmful side effects, provided that such higher dose levels are first divided into several small doses for administration throughout the day.

The pharmaceutically active agents used in the methods and pharmaceutical compositions of this invention can be administered orally, parenterally, or topically, alone or in combination with pharmaceutically acceptable carriers or diluents, and such administration may be carried out in single or multiple doses. More particularly, the therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a pharmaceutically active agent used in accordance with this invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well known to those skilled in the art.

Additionally, it is also possible to administer the active agents used in accordance with the present invention topically, and this may be done by way of creams, jellies, gels, pastes, patches, ointments and the like, in accordance with standard pharmaceutical practice.

Certain NMDA antagonists of the formula I are illustrated by the following examples.

All nonaqueous reactions were run under nitrogen for convenience and generally to maximize yields. All solvents/diluents were dried according to standard published procedures or purchased in a predried form. All reactions were stirred either magnetically or mechanically. NMR spectra are recorded at 300 MHz and are reported in ppm. The NMR solvent was $CDCl_3$ unless otherwise specified. IR spectra are reported in $cm^{-1}$, generally specifying only strong signals.

EXAMPLE 1

Enantiomeric (1S, 2S)- and (1R, 2R)-1-(4-Hydroxyphenyl)-2-(4-hydroxy-4-phenylpiperidin-1-yl)-1-propanol (+)-Tartaric acid (300 mg, 2 mmol) was dissolved in 30 mL warm methanol. Racemic 1S*, 2S*-1-(4-hydroxyphenyl)-2-(4-hydroxy-4-phenyl piperidin-1-yl)-1-propanol (655 mg, 2 mmol) was added all at once. With stirring and gentle warming a colorless homogeneous solution was obtained. Upon standing at ambient temperature 24 hours, 319 mg (66%) of a fluffy white precipitate was obtained. This product was recrystallized from methanol to give 263 mg of the (+)-tartrate salt of levorotatory title product as a white solid; mp 206.5–207.5° C.; [alpha]$_D$=−36.2°. This salt (115 mg) was added to 50 mL of saturated $NaHCO_3$. Ethyl acetate (5 mL) was added and the mixture was vigorously stirred 30 minutes. The aqueous phase was repeatedly extracted with ethyl acetate. The organic layers were combined and washed with brine, dried over calcium sulfate, and concentrated. The tan residue was recrystallized from ethyl acetate-hexane to give 32 mg (39%) of white, levorotatory title product; mp 203–204° C.; [alpha]$_D$=−58.4°. Anal. Calc'd. for $C_{20}H_{25}NO_3$: C, 73.37; H, 7.70; N, 4.28. Found: C, 72.61; H, 7.45; N, 4.21.

The filtrate from the (+)-tartrate salt preparation above was treated with 100 mL saturated aqueous $NaHCO_3$ and extracted well with ethyl acetate. The combined organic extracts were washed with brine, dried over calcium sulfate and concentrated to give 380 mg of recovered starting material (partially resolved). This material was treated with (−)-tartaric acid (174 mg) in 30 mL of methanol as above. After standing for 24 hours, filtration gave 320 mg (66%) of product which was further recrystallized from methanol to produce 239 mg of the (−)-tartrate salt of dextrorotatory title product; mp 206.5–207.5° C. [alpha]$_D$=+33.9°. The latter was converted to dextrorotatory title product in the manner above in 49% yield; mp 204–205° C.; [alpha]$_D$=+56.90. Anal. Found: C, 72.94; H, 7.64; N, 4.24.

EXAMPLE 2

(1S, 2S)-1-(4-hydroxyphenyl)-2-(4-hydroxy-4-phenylpiperidin-yl)-1-propanol methanesulfonate trihydrate

STEP 1

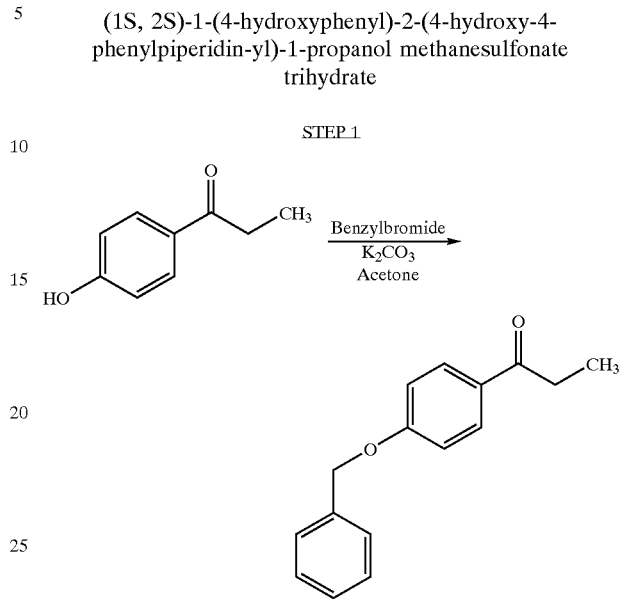

A 50 gallon glass lined reactor was charged with 17.1 gallons of acetone, 8.65 kilograms (kg) (57.7 mol) of 4'-hydroxypropiophenone, 9.95 kg (72.0 mol) of potassium carbonate and 6.8 liters (L) (57.7 mol) of benzylbromide. The mixture was heated to reflux (56° C.) for 20 hours. Analysis of thin layer chromatography (TLC) revealed that the reaction was essentially complete. The suspension was atmospherically concentrated to a volume of 10 gallons and 17.1 gallons of water were charged. The suspension was granulated at 25° C. for 1 hour. The product was filtered on a 30" Lapp and washed with 4.6 gallons of water followed by a mixture of 6.9 gallons of hexane and 2.3 gallons of isopropanol. After vacuum drying at 45° C., this yielded 13.35 kg (96.4%) of the above-depicted product.

A second run was carried out with 9.8 kg (65.25 mol) of 4'-hydroxypropiophenone using the procedure described above. After drying 15.1 kg (96.3%) of the above-depicted product was obtained.

STEP 2

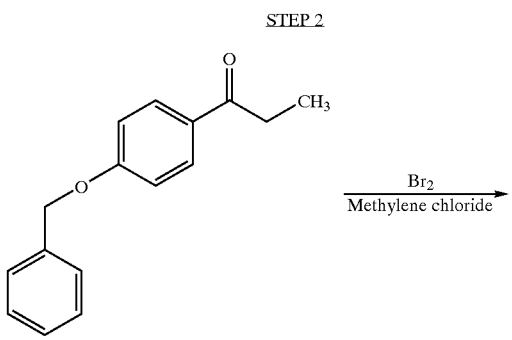

-continued

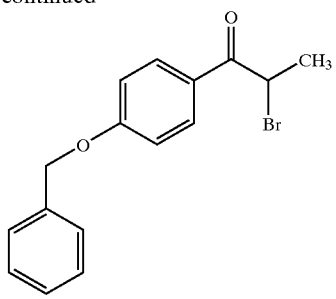

Under a nitrogen atmosphere, a 100 gallon glass lined reactor was charged with 75 gallons of methylene chloride and 28.2 kg (117.5 mol) of the product from step 1. The solution was stirred five minutes and then 18.8 kg of bromine was charged. The reaction was stirred for 0.5 hours at 22° C. Analysis of TLC revealed that the reaction was essentially complete. To the solution was charged 37 gallons of water and the mixture was stirred for 15 minutes. The methylene chloride was separated and washed with 18.5 gallons of saturated aqueous sodium bicarbonate. The methylene chloride was separated, atmospherically concentrated to a volume of 40 gallons and 60 gallons of isopropanol was charged. The concentration was continued until a pot temperature of 80° C. and final volume of 40 gallons were obtained. The suspension was cooled to 20° C. and granulated for 18 hours. The product was filtered on a 30" Lapp and washed with 10 gallons of isopropanol. After vacuum drying at 45° C., this yielded 29.1 kg (77.6%) of the above-depicted product.

STEP 3

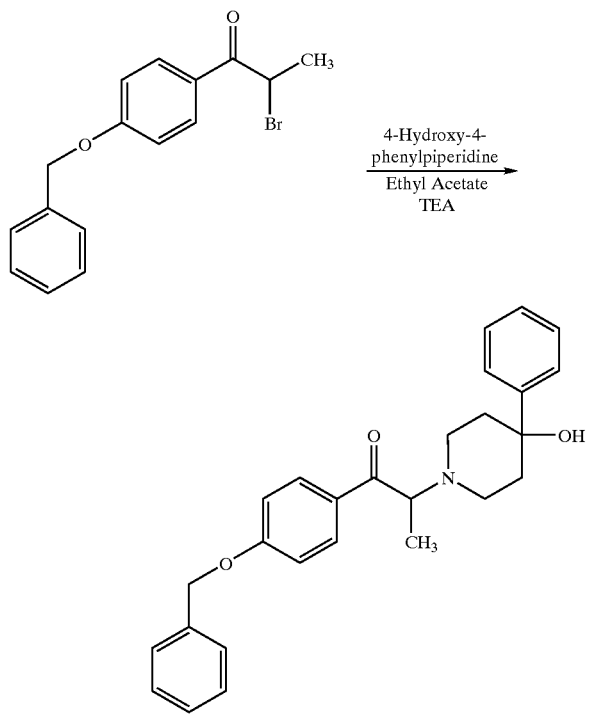

Under a nitrogen atmosphere, a 20 gallon glass lined reactor was charged with 4.90 kg (15.3 mol) of the product from step 2, 7.0 gallons of ethyl acetate, 2.70 kg (15.3 mol) of 4-hydroxy-4-phenylpiperidine and 1.54 kg of triethylamine (15.3 mol). The solution was heated to reflux (77° C.) for 18 hours. The resulting suspension was cooled to 20° C. Analysis by TLC revealed that the reaction was essentially complete. The byproduct (triethylamine hydrobromide salt) was filtered on a 30" Lapp and washed with 4 gallons of ethyl acetate. The filtrate was concentrated under vacuum to a volume of 17 liters. The concentrate was charged to 48 liters of hexane and the resulting suspension granulated for 2 hours at 20° C. The product was filtered on a 30" Lapp and washed with 4 gallons of hexane. After vacuum drying at 50° C., this yielded 4.9 kg (77%) of the above-depicted product.

A second run was carried out with 3.6 kg (11.3 mol) of the product from step 2 using the procedure described above. After drying 4.1 kg (87%) of the above-depicted product was obtained.

STEP 4

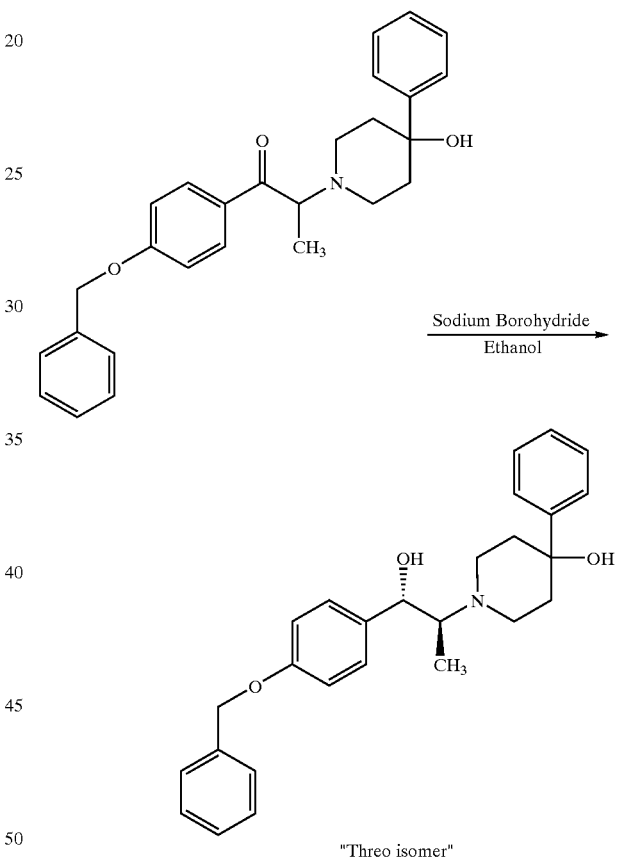

"Threo isomer"

Under a nitrogen atmosphere, a 100 gallon glass lined reactor was charged with 87.0 gallons of 2B ethanol and 1.7 kg (45.2 mol) of sodium borohydride. The resulting solution was stirred at 25° C. and 9.4 kg (22.6 mol) of the product from step 3 was charged. The suspension was stirred for 18 hours at 25–30° C. Analysis by TLC revealed that the reaction was essentially complete to the desired threo diastereoisomer. To the suspension was charged 7.8 liters of water. The suspension was concentrated under vacuum to a volume of 40 gallons. After granulating for 1 hour, the product was filtered on a 30" Lapp and washed with 2 gallons of 2B ethanol. The wet product, 9.4 gallons of 2B-ethanol and 8.7 gallons of water were charged to a 100 gallon glass lined reactor. The suspension was stirred at reflux (78° C.) for 16 hours. The suspension was cooled to 25° C., filtered on 30" Lapp and washed with 7 gallons of water followed by 4 gallons of 2B ethanol. After air drying at 50° C., this yielded 8.2 kg (86.5%) of the above-depicted product. This material was recrystallized in the following manner.

A 100 gallon glass lined reactor was charged with 7.9 kg (18.9 mol) of the product from step 3, 20 gallons of 2B ethanol and 4 gallons of acetone. The suspension was heated to 70° C. producing a solution. The solution was concentrated atmospherically to a volume of 15 gallons. The suspension was cooled to 25° C. and granulated for 1 hour. The product was filtered on a 30" Lapp. The wet product and 11.7 gallons of 2B ethanol was charged to a 100 gallon glass lined reactor. The suspension was heated to reflux (78° C.) for 18 hours. The suspension was cooled to 25° C., filtered on a 30" Lapp and washed with 2 gallons of 2B ethanol. After air drying at 50° C. this yielded 5.6 kg (70.6%) of the above-depicted product.

STEP 5

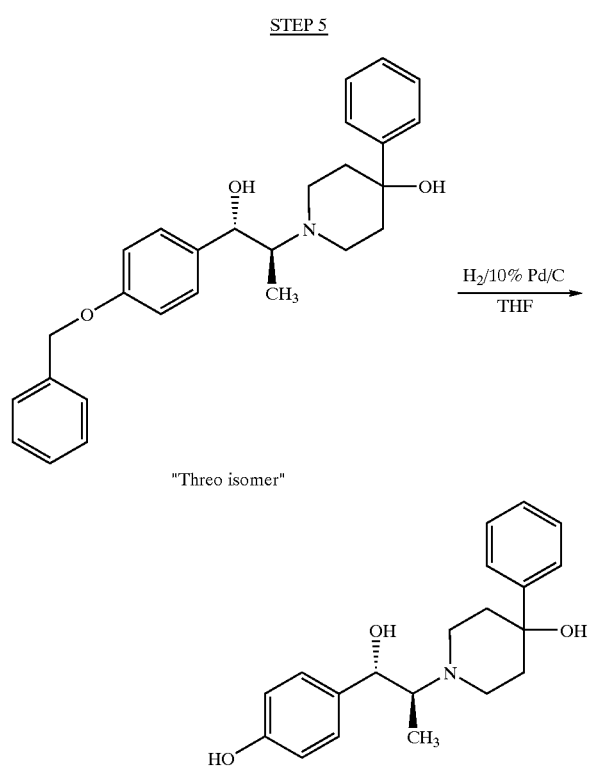

"Threo isomer"

Under a nitrogen atmosphere, a 50 gallon glass lined reactor was charged with 825 g of 10% palladium on carbon (50% water wet), 5.5 kg (13.2 mol) of the product from step 4 and 15.5 gallons of tetrahydrofuran (THF). The mixture was hydrogenated between 40–50° C. for 2 hours. At this time, analysis by TLC revealed that the reduction was essentially complete. The reaction was filtered through a 14" sparkler precoated with Celite and washed with 8 gallons of THF. The filtrate was transferred to a clean 100 gallon glass lined reactor, vacuum concentrated to a volume of 7 gallons and 21 gallons of ethyl acetate were charged. The suspension was atmospherically concentrated to a volume of 10 gallons and a pot temperature of 72° C. The suspension was cooled to 10° C., filtered on a 30" Lapp and washed with 2 gallons of ethyl acetate. After air drying at 55° C. this yielded a 3.9 kg (90%) of the above-depicted product (i.e., the free base).

STEP 6

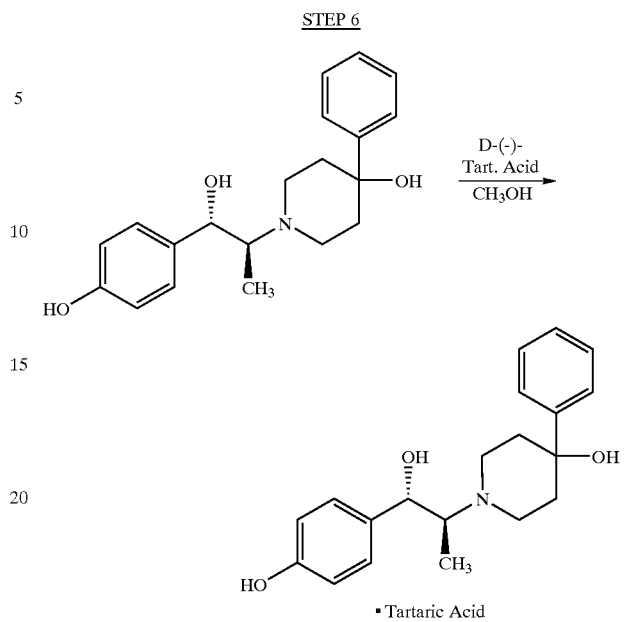

A 100 gallon glass lined reactor was charged with 20 gallons of methanol and 3.7 kg (11.4 mol) of the product from step 5 (i.e., the free base). The suspension was heated to 60° C. and 1.7 kg (11.4 mol) of D-(-)-tartaric acid were charged. The resulting solution was heated to reflux (65° C.) for 3 hours after which a suspension formed. The suspension was cooled to 35° C., filtered on a 30" Lapp and washed with 1 gallon of methanol. The wet solids were charged to a 100 gallon glass lined reactor with 10 gallons of methanol. The suspension was stirred for 18 hours at 25° C. The suspension was filtered on a 30" Lapp and washed with 2 gallons of methanol. After air drying at 50° C. this yielded 2.7 kg (101%) of the above-depicted product (i.e., the tartaric acid salt of the free base (R-(+)-enantiomer)). This material was purified in the following manner:

A 100 gallon glass lined reactor was charged with 10.6 gallons of methanol and 2.67 kg (5.6 mol) of the above tartaric acid salt. The suspension was heated to reflux (80° C.) for 18 hours. The suspension was cooled to 30° C., filtered on a 30" Lapp and washed with 4 gallons of methanol. After air drying at 50° C., this yielded 2.05 kg (76.7%) of the above-depicted product (i.e., the tartaric acid salt of the free base).

STEP 7

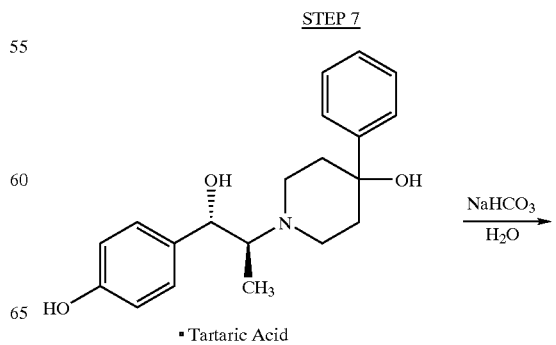

-continued

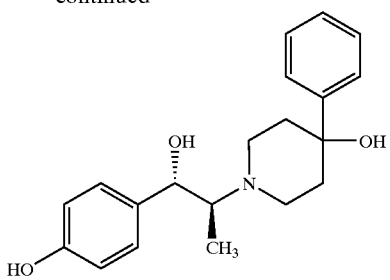

A 55 liter nalgene tub was charged with 30 liters of water and 1056 g (12.6 mol) of sodium bicarbonate at 20° C. To the resulting solution was charged 2.0 kg (4.2 mol) of the product from step 6 (i.e., the tartaric acid salt of the free base). The suspension was stirred for 4 hours during which a great deal foaming occurred. After the foaming ceased, the suspension was filtered on a 32 cm funnel and washed with 1 gallon of water. After air drying at 50° C., this yielded 1.28 kg (93.5%) of the above-depicted product (i.e., the free base).

STEP 8

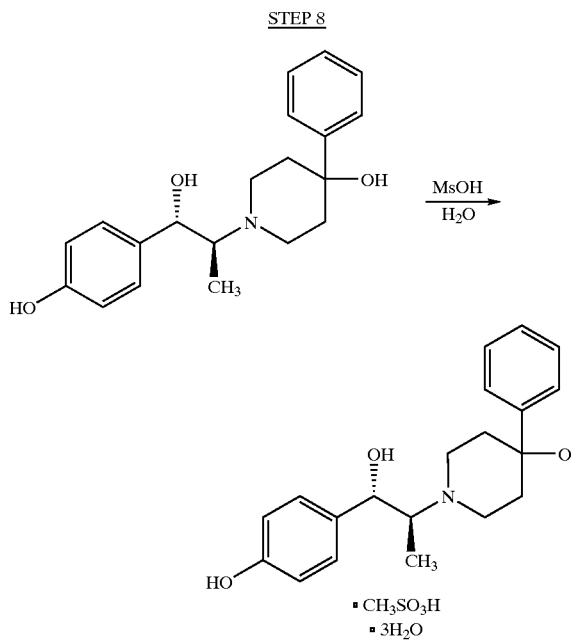

A 22 liter flask was charged with 1277 g (3.9 mol) of product from step 7 and 14 liters of water. The suspension was warmed to 30° C. and 375 g (3.9 mol) of methane sulfonic acid were charged. The resulting solution was warmed to 60° C., clarified by filtering through diatomaceous earth (Celite™) and washed with 2 liters of water. The speck-free filtrate was concentrated under vacuum to a volume of 6 liters. The suspension was cooled to 0–5° C. and granulated for 1 hour. The product was filtered on an 18" filter funnel and washed with 635 ml of speck-free water. After air drying at 25° C. for 18 hours, this yielded 1646 g (88%) of the above-depicted product (i.e., the mesylate salt trihydrate).

EXAMPLE 3

(1R*, 2R*)-1-(4-hydroxy-3-methylphenyl)-2-(4-(4-fluorophenyl)-4-hydroxypiperidin-1-yl-propan-1-ol-mesylate A mixture of 3-methyl-4-triisopropylsilyloxy-α-bromopropiophenone (9.17 g, 22.97 mmol), 4-(4-fluorophenyl)-4-hydroxypiperidine (6.73 g, 34.45 mmol) and triethylamine (8.0 mL, 57.43 mmol) in in ethanol (180 mL) was refluxed for 6 hours. The solvent was removed at reduced pressure and the residue was partitioned between ethyl acetate and water. The phases were separated and the organic layer was washed with brine, dried over calcium sulfate and concentrated. The residue was flash chromatographed on silica gel (3×3.5 inches packed in hexane) with elution proceeding as follows: 10% ethyl acetateihexane (100 mL), nil; 20% ethyl acetate/hexane (700 mL), nil; 20% ethyl acetateihexane (1300 mL) and 25% ethyl acetate/hexane (600 mL), 7.66 g (65%) of 1-(3-methyl-4-triisopropylsilyloxyphenyl)-2-(4-(4-fluorophenyl)-4-hydroxypiperidin-1-yl)-propan-1-one as a yellow foam which was suitable for use without further purification. A sample recrystallization from ethyl acetateihexane as white crystals had: m.p. 78–82° C.

A mixture of sodium borohydride (0.564 g, 14.92 mmol) and ethanol (60 mL) was stirred 10 minutes and then 1-(3-methyl-4-triisopropylsilyloxyphenyl)-2-(4-(4-fluorophenyl)-4-hydroxypiperidin-1-yl)-propan-1-one (7.66 g, 14.92 mmol in 10 mL of ethanol) was added with two 30 mL ethanol rinses. The reaction mixture was stirred at ambient temperature overnight. The white solid that precipitated was collected by filtration and dried to yield 5.72 g (74%) of (1R*, 2R*)-1-(3-methyl-4-triisopropylsilyloxyphenyl)-2-(4-(4-fluorophenyl)-4-hydroxypiperidin-1-yl-propan-1-ol, which was suitable for use without further purification and had: m.p. 188–189° C.

The product of the above reaction (5.72 g, 11.1 mmol) was dissolved in tetrahydrofuran (150 mL) and tetrabutylammonium fluoride (12.21 mL, 12.21 mmol, 1M tetrahydrofuran solution) was added. The reaction was stirred 1 hour at ambient temperature and then concentrated. The residue was partitioned between ethyl acetate and water and the two phases were separated. The organic layer was slurried with methylene chloride. The white solid that precipitated was collected by filtration and dried to afford 3.41 g (85%) of (1R*, 2R*)-1-(4-hydroxy-3-methylphenyl)-2-(4-(4-fluorophenyl)-4-hydroxypipeidin-1-yl)-propan-1-ol. A sample (0.16 g, 0.447 mmol) was converted to the corresponding mesylate salt. The salt was slurried in methanol (8 mL) and methanesulfonic acid (0.029 mL, 0.45 mmol) was added. The mixture was filtered and concentrated. The mixture was then recrystallized from ethanol to give 0.152 g (58%) of the mesylate salt which had: m.p. 215–216° C. Analysis calculated for $C_{21}H_{25}FNO_3 \cdot CH_4SO_3$: C, 58.01; H, 6.64, N, 3.07. Found: C, 57.99; H, 6.72: N, 317

EXAMPLE 4

1R, 2R 1-(4-hydroxy-3-methoxyphenyl)-2-(4-hydroxy-4-phenyl-piperidin-1-yl)-propan-1-ol and 1S, 2S 1-(4-hydroxy-3-methoxyphenyl)-2-(4-hydroxy-4-phenyl-piperidin-1-yl)-propan-1-ol A mixture of 2-bromo-1-(2,2-diphenyl-benzo(1,3)dioxol-5-yl)-propan-1-one (2.00 g, 4.89 mmol), 4-hydroxy-4-phenylpiperidine (0.9 g, 5.08 mmol) and triethylamine (1.40 mL, 10.04 mmol) in ethanol (50 mL) was refluxed overnight. The solvent was removed at reduced pressure and the residue was partitioned between ether and water. The phases were separated and the organic layer was washed with brine, dried over magnesium sulfate and concentrated. The residue was flash chromatographed on silica gel (2×5 inches packed with hexane) with elution proceeding as follows: 20% ethyl acetate/hexane (500 mL), unweighed forerun; 50% ethyl acetate/hexane (500 mL), 1.76 g (71%) of 1-(2,2)-diphenyl-benzo(1,3)dioxol-5-yl)-2-(4-hydroxy-4-phenylpiperidin-1-yl)-propan-1-one as light tan foam which was suitable for use without further purification and had: NMR δ 7.81 (dd, J=1.7, 8.3 Hz, 1H), 7.70 (d, J=1.6 Hz, 1H), 7.64–7.13 (m, 15H), 6.92 (d, J=8.2 Hz, 1H), 4.07 (q, J=7.0 Hz, 1H), 3.39–3.27 (m, 1H), 2.94–2.59 (m, #H), 2.30–2.04 (m, 2H), 1.74 (br t, J=13.2 Hz, 2H), 1.30 (d, J=6.8 Hz, 3H).

A mixture of sodium borohydride (0.15 g, 3.97 mmol) and ethanol (5 mL) was stirred 10 minutes and then 1-(2,2-diphenyl-benzo(1,3)dioxol-5-yl)-2-(4-hydroxy-4-phenylpiperidin-1-yl)-propan-1-one (1.70 g, 3.36 mmol in 20 mL of ethanol) was added. The reaction was stirred at ambient temperature over the weekend. The white precipitate was collected, rinsed with ethanol and ether and air dried to afford 1.35 g of crude product. The product was recrystallized from ethanol/ethyl acetate/methylene chloride to give 1.05 g (61%) of 1R*, 2R*)-1-(2,2-diphenyl-benzo(1,3)dioxol-5-yl)-2-(4-hydroxy-4-phenylpiperidin-1-yl)-propan-1-ol which had: mp 224–224.5° C. Analysis calculated for $C_{33}H_{33}NO_4$: C, 78.08; H, 6.55; N, 2.76. Found: C, 78.16; H, 6.46; N, 2.72.

A mixture of the product of the above reaction (1.00 g, 1.97 mmol) and 10% palladium on carbon (0.175 g) in methanol (50 mL) and acetic acid (1.0 mL) was hydrogenated at 50 psi (initial pressure) for 5 hours at ambient temperature. Additional catalyst (0.18 g) was added and the hydrogenation was continued overnight. The reaction was filtered through diatomaceous earth and the filter pad was rinsed with methanol. The filtrate was concentrated and the residue was partitioned between ethyl acetate and saturated aqueous bicarbonate and stirred vigorously for 1 hour. The phases were separated and the aqueous layer was extracted with ethyl acetate (2×). The combined organic layer was washed with water and brine, dried over magnesium sulfate and concentrated. The residue was flash chromatographed on silica gel (1×4 inches) with elution proceeding as follows: 20% ethyl acetate/hexane (500 mL), nil; 10% methanol/ethyl acetate (250 mL), 20% methanol/ethyl acetate (250 mL), and 50% methanol/ethyl acetate, 0.51 g (75%) of a light yellow-green solid. The solid was recrystallized from ethanol to afford (1R*, 2R*)-1-(3,4-dihydroxyphenyl)-2-(4-hydroxy-4-phenyl-piperidin-1-yl)-propan-1-ol as a white solid which had: mp 167–168° C. Analysis calculated for $C_{20}H_{25}NO_4 \cdot 0.5\ C_2H_6O$: C, 68.83; H, 7.70; N, 3.82. Found: C, 68.78; H, 8.05; N, 3.70.

The racemic product was dissolved in ethanol and separated into enantiomers by HPLC using the following chromatographic conditions: Column, Chiralcel OD; mobile phase, 25% ethanol/75% hexane; temperature, ambient (approximately 22° C.); detection, UV at 215 nM. Under these conditions, 1R, 2R 1-(4-hydroxy-3-methoxyphenyl)-2-(4-hydroxy-4-phenyl-piperidin-1-yl) propan-1-ol eluted with a retention time of approximately 9.12 minutes and 1S, 2S 1-(4-hydroxy-3-methoxyphenyl)-2-(4-hydroxy-4-phenyl-piperidin-1-yl) propan-1-ol eluted with a retention time of approximately 16.26 minutes.

EXAMPLE 5

(3R*, 4S*)-3-(4-(4-fluorophenyl)-4-hydroxypiperidin-1-yl)-chroman-4,7-diol

A mixture of 7-benzyloxy-3,3-dibromochromanone (54.7 g, 133 mmol), 4-(4-fluorophenyl)-4-hydroxypiperidine (52.0 g, 266 mmol), and triethylamine (38 mL, 270 mmol) in acetonitrile (2.5L) was stirred 16 hours at ambient temperature. A yellow precipitate formed and was collected, washed well with water and ether, and air dried. The yield of 7-benzyloxy-3-{4-(4-fluorophenyl)-4-hydroxy-pipridine-1-yl]-chromenone was 55.4 g (93%) which was suitable for use without further purification. A sample recrystallized from ethanol/tetrahydrofuran had mp 220–221° C.: NMR $DMSO_{d_6}$ δ7.99 (d, J=9 Hz, 2H), 7.56–7.40 (m, 8H), 7.18–7.08 (m, 4H), 5.25 (s, 2H), 5.06 (s, 1H), 3.60 (br s, 1H), 3.55 (m, 1H, partially obscured by water from the NMR solvent), 3.10–2.95 (m, 2H), 2.15–2.00 (m, 2H), 1.71 (br t, J=13.7 Hz, 2H).

Analysis calculated for $C_{27}H_{24}FNO_4$: C, 72.80; H, 5.43; N, 3.13. Found: C, 72.83; H, 5.82; N, 2.82.

To a slurry of 7-benzyloxy-3-[4-(4-fluorophenyl)-4-hydroxy-piperidine-1-yl]-chromenone (8.24 g, 18.5 mmol) in ethanol (400 mL) and tetrahydrofuran (600 mL) was added sodium borohydride (7.0 g, 185 mmol). The mixture was stirred overnight. Additional sodium borohydride (7.0 g) was added and the reaction mixture was stirred for 3 days. Water was added and the solvent was removed at reduced pressure at 45° C. The solids which formed were collected and washed well with water and then ether. The solid was further dried in vacuo overnight to give 5.01 g, 60% of 3R* 4S* 7-benzyloxy-3-[4-(4-fluorophenyl)-4-hydroxy-piperidin-1-yl]-chroman-4-ol which was suitable for use without further purification. A sample recrystallized from ethyl acetate/chloroform had mp. 194–195° C.; NMR δ7.56–7.30 (m, 8H), 7.06 (long range coupled t, J=8.7 Hz, 2H) 6.63 (dd, J=2.4, 8.5 Hz, 1H), 6.47 (d, J=2.4 Hz, 1H), 5.04 (s, 2H), 4.77 (d, J=4.5 Hz, 1H), 4.37 (dd, J=3.5, 10.4 Hz, 1H), 4.13 (t, J=10.4 Hz, 1H),3.82 (brs, 1H), 3.11 (br d, J=11.2 Hz, 1H), 2.92–2.71 (m, 4H), 2.21–2.06(m, 2H), 1.87–1.73 (m, 2H), 1.54 (s, 1H).

Analysis calculated for $C_{27}H_{28}FNO_4$: C, 72.14; H, 6.28; N, 3.12. Found C, 72.15; H, 6.21; N, 3.12.

A mixture of 3R* 4S* 7-benzyloxy-3-[4-(4-fluorophenyl)-4-hydroxy-piperidin-1-yl]-chroman-4-ol (0.80 g, 1.78 mmol), 10% palladium on carbon (0.16 g), methanol (40 mL), and acetic acid (0.8 mL) was hydrogenated for 8 hours with a starting pressure of 48.5 psi. The reaction was filtered through celite and the filtrate was concentrated. The residue was stirred vigorously with ether and saturaturated sodium bicarbonate for 1 hour. The solid was washed with water and ether and dried in vacuo. Recrystallization from ethanol yielded 0.35 g (54%) of 3R* 4S* 3-[4-(4-fluorophenyl)-4-hydroxy-piperidin-1-yl]-chroman-4,7-diol as a white solid which had mp 159–160° C.; NMR $DMSO_{d_6}$ δ7.55–7.47 (m, 2H), 7.11 (t, J=9 Hz, 2H), 7.02 (d, J=8.4 Hz, 1H)k, 6.32 (dd, J=2.3, 8.3 Hz, 1H), 6.15 (d, J=2.3 Hz 1H), 5.10–4.50 (br m with s at 4.63, 3H), 4.23 (dd, J=2.8, 10.3 Hz, 1H),2.99 (br d, J=10.8 Hz, 1H), 2.86 (br d, J=10.7 Hz, 1H), 2.73–2.50 (m, 3H), 2.08–1.90 (m, 2H), 1.58 (br d, J=13 Hz, 2H).

Analysis calculated for $C_{20}H_{22}FNO_4 \cdot 0.25H_2O$; C, 66.01; H, 6.23; N, 3.85. Found: C, 66.22; H, 6.58; N. 3.46.

TABLE 1

Affinity of Compound A and other compounds for displacement of the specific binding of racemic [$^3$H] (+)-(1S, 2S)-1-(4-hydroxy-phenyl)-2-(4-hydroxy-4-phenylpiperidino)-1-propanol or [$^3$H]Prazosin to rat forebrain membranes.

| Compound | Racemic [$^3$H] (+)-(1S, 2S)-1-(4-hydroxy-phenyl)-2-(4-hydroxy-4-phenylpiperidino)-1-propanol binding (nM) | [$^3$H]Prazosin binding (nM) | Ratio [$^3$H]Prazosin/ [$^3$H] (+)-(1S, 2S)-1-(4-hydroxy-phenyl)-2-(4-hydroxy-4-phenylpiperidino)-1-propanol |
|---|---|---|---|
| (+)-(1S, 2S)-1-(4-hydroxy-phenyl)-2-(4-hydroxy-4-phenylpiperidino)-1-propanol | 13 ± 4 | 19,500 ± 5,000 | 1,500 |
| (1R*, 2R*)-1-(4-hydroxy-3-methylphenyl)-2-(4-(4-fluorophenyl)-4-hydroxypiperidin-1-yl)-propan-1-ol-mesylate | 14 ± 2.1 | 10,000 | 714 |
| (1S, 2S)-1-(4-hydroxy-3-methoxyphenyl)-2-(4-hydroxy-4-phenylpiperidino)-1-propanol | 94 | 8100 | 86 |
| (3R, 4S)-3-(4-(4-fluorophenyl)-4-hydroxypiperidin-1-yl)-chroman-4,7-diol | 18 ± 3 | >10,000 | ≧555 |
| Ifenprodil (Comparative) | 70 ± 25 | 114 ± 5 | 1.6 |
| Eliprodil (Comparative) | 450 ± 130 | 980 ± 220 | 2.2 |

What is claimed is:

1. A pharmaceutical composition for treating hypoxic or ischemic stroke in a mammal, comprising:
   (a) a thrombolytic agent or a pharmaceutically acceptable salt thereof;
   (b) an NR2B subtype selective NMDA receptor antagonizing compound or a pharmaceutically acceptable salt thereof; and
   c) a pharmaceutically acceptable carrier;
   wherein the active agents "a" and "b" are present in such composition in amounts that render the combination of the two agents effective in treating such disorder.

2. A pharmaceutical composition according to claim 1, wherein the thrombolytic agent that is employed in such composition is selected from tissue plasminogen activator (TPA), urokinase, prourokinase and streptokinase.

3. A method of treating hypoxic or ischemic stroke in a mammal, comprising administering to said mammal:
   (a) a thrombolytic agent or a pharmaceutically acceptable salt thereof; and
   (b) an NR2B subtype selective NMDA receptor antagonizing compound or a pharmaceutically acceptable salt thereof;
   wherein the active agents "a" and "b" above are present in amounts that render the combination of the two agents effective in treating hypoxic or ischemic stroke.

4. A method according to claim 3, wherein the thrombolytic agent that is employed in such method is selected from tissue plasminogen activator (TPA), urokinase, prourokinase and streptokinase.

5. The method of claim 3, wherein said NMDA receptor antagonist is an NR2B selective NMDA receptor antagonist of the formula

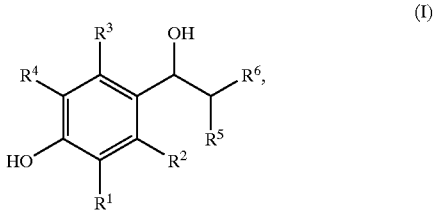

(I)

or a pharmaceutically acceptable acid addition salt thereof, wherein:

(a) $R^2$ and $R^5$ are taken separately and $R^1$, $R^2$, $R^3$ and $R^4$ are each independently hydrogen, ($C_1$–$C_6$) alkyl, halo, $CF_3$, OH or $OR^7$ end $R^5$ is methyl or ethyl; or (b) $R^2$ and $R^5$ are taken together and are

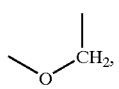

forming a chroman-4-ol ring, and $R^1$, $R^3$ and $R^4$ are each independently hydrogen, ($C_1$–$C_6$) alkyl, halo, $CF_3$, OH or $OR^7$;

R⁶ is

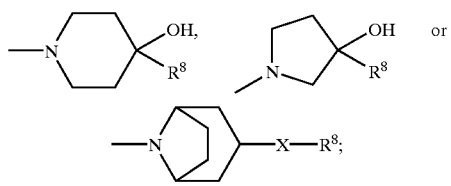

R⁷ is methyl, ethyl, isopropyl or n-propyl;
R⁸ is phenyl optionally substituted with up to three substituents independently selected from the group consisting of ($C_1$–$C_6$) alkyl, halo and $CF_3$;
X is O, S or $(CH_2)_n$; and
n is 0, 1, 2, or 3.

6. The method of claim 5, wherein said NR2B subtype selective NMDA receptor antagonist is (+)-(1S, 2S)-1-(4-hydroxy-phenyl)-2-(4-hydroxy-4-phenylpiperidino)-1-propanol or a pharmaceutically acceptable acid addition salt thereof.

7. The method of claim 5, wherein said NR2B subtype selective NMDA receptor antagonist is (1S, 2S)-1-(4-hydroxy-3-methoxyphenyl)-2-(4-hydroxy-4-phenylpiperidino)-1-propanol or a pharmaceutically acceptable acid addition salt thereof.

8. The method of claim 5, wherein said NR2B subtype selective NMDA receptor antagonist is (3R,4S)-3-(4-(4-fluorophenyl)-4-hydroxypiperidin-1-yl)-chroman-4,7-diol or a pharmaceutically acceptable acid addition salt thereof.

9. The method of claim 5, wherein said NR2B subtype selective NMDA receptor antagonist is (1R*, 2R*)-1-(4-hydroxy-3-methylphenyl)-2-(4-(4-fluorophenyl)-4-hydroxypiperidin-1-yl)-propan-1-ol-mesylate.

10. The method of claim 3, wherein the NR2B subtype selective NMDA receptor antagonist has a ratio of NR2B receptor activity to $\alpha_1$-adrenergic receptor activity that is at least about 3:1.

11. The method of claim 3, wherein the NMDA receptor antagonist has a ratio of NR2B receptor activity to $\alpha_1$-adrenergic receptor activity that is at least about 5:1.

* * * * *